(12) United States Patent
Jaeschke et al.

(10) Patent No.: US 11,117,890 B2
(45) Date of Patent: Sep. 14, 2021

(54) SUBSTITUTED ISOINDOLE ALLOSTERIC EGFR INHIBITORS

(71) Applicant: Hoffmann-La Roche Inc., Little Falls, NJ (US)

(72) Inventors: Georg Jaeschke, Basel (CH); Antonio Ricci, Basel (CH); Daniel Rueher, Basel (CH); Sandra Steiner, Basel (CH); Martin Duplessis, Watertown, MA (US); Yvonne Alice Nagel, Basel (CH); Bernd Kuhn, Basel (CH)

(73) Assignee: Hoffman La-Roche Inc., Little Falls, NJ (US)

( * ) Notice: Subject to any disclaimer, the term of this patent is extended or adjusted under 35 U.S.C. 154(b) by 0 days.

(21) Appl. No.: 16/700,900

(22) Filed: Dec. 2, 2019

(65) Prior Publication Data

US 2020/0102299 A1    Apr. 2, 2020

Related U.S. Application Data

(63) Continuation of application No. PCT/EP2018/064399, filed on Jun. 1, 2018.

(60) Provisional application No. 62/514,244, filed on Jun. 2, 2017, provisional application No. 62/543,438, filed on Aug. 10, 2017.

(30) Foreign Application Priority Data

Jun. 2, 2017 (EP) .................................... 17174334

(51) Int. Cl.
*C07D 417/14* (2006.01)
*C07D 417/12* (2006.01)
*A61P 35/04* (2006.01)

(52) U.S. Cl.
CPC ............ *C07D 417/14* (2013.01); *A61P 35/04* (2018.01); *C07D 417/12* (2013.01)

(58) Field of Classification Search
CPC ... C07D 417/12; C07D 417/14; C07D 403/14
See application file for complete search history.

(56) References Cited

FOREIGN PATENT DOCUMENTS

| CN | 102060848 A | 5/2011 |
| CN | 102093339 A | 6/2011 |
| WO | WO 2007/143434 A2 | 12/2007 |
| WO | WO 2009/158369 A1 | 12/2009 |
| WO | WO 2011/128279 A1 | 10/2011 |
| WO | WO 2016/183534 A1 | 11/2016 |

OTHER PUBLICATIONS

Cheng Y and W H Prusoff, "Relationship between the inhibition constant (K1) and the concentration of inhibitor which causes 50 per cent inhibition (I50) of an enzymatic reaction", Biochem Pharmacol., Dec. 1, 1973, 22(23):3099-108. doi: 10.1016/0006-2952(73)90196-2.

Ciardiello, F., and Tortora, G., "EGFR antagonists in cancer treatment", The New England journal of medicine, 2008, 358, 1160-1174.

International Search Report and Written Opinion for PCT/EP2018/064399 dated Sep. 14, 2018.

Jia et al., "Overcoming EGFR(T790M) and EGFR(C797S) resistance with mutant-selective allosteric inhibitors", Nature, Jun. 2016, 534, 129-132.

Li H Q et al., "Synthesis and structure-activity relationships of N-benzyl-N-(X-2-hydroxybenzyl)-N-phenylureas and thioureas as antitumor agents", Bioorganic and Medicinal Chemistry, 2010, 18(1), 305-313, XP026810721.

Paez, J. et al., "EGFR mutations in lung cancer: correlation with clinical response to gefitinib therapy", Science, 2004, (New York, NY 304, 1497-1500.

Sharma SV, Bell DW, Settleman J, Haber DA., "Epidermal growth factor receptor mutations in lung cancer", Nat Rev Cancer, Mar. 2007;7(3): 169-81.

Thress, K. S. et al., "Acquired EGFR C797S mutation mediates resistance to AZD9291 in non-small cell lung cancer harboring EGFR T790M", Nat. Med., 2015, 21, 560-562.

Wang et al., "EGFR C797S mutation mediates resistance to third-generation inhibitors in T790M-positive non-small cell lung cancer", J Hematol Oncol., 2016, 9: 59.

Yang et al, "Investigating Novel Resistance Mechanisms to Third-Generation EGFR Tyrosine Kinase Inhibitor Osimertinib in Non-Small Cell Lung Cancer Patients", Clin Cancer Res., Jul. 1, 2018;24(13):3097-3107. doi: 10.1158/1078-0432.CCR-17-2310.

Yarden, Y., Sliwkowski, MX., "Untangling the ErbB signalling network", Nature Review Mol Cell Biol., Feb. 2001, 2(2): 127-37.

US, 2019/0308955, A1, U.S. Appl. No. 16/449,040, Duplessis et al, Oct. 10, 2019.

*Primary Examiner* — Susanna Moore
(74) *Attorney, Agent, or Firm* — Knowles Intellectual Property Strategies, LLC

(57) ABSTRACT

The present invention provides substituted isoindole compounds which are selective allosteric EGFR inhibitors, their manufacture, pharmaceutical compositions containing them and their use as therapeutically active substances, generally of Formula:

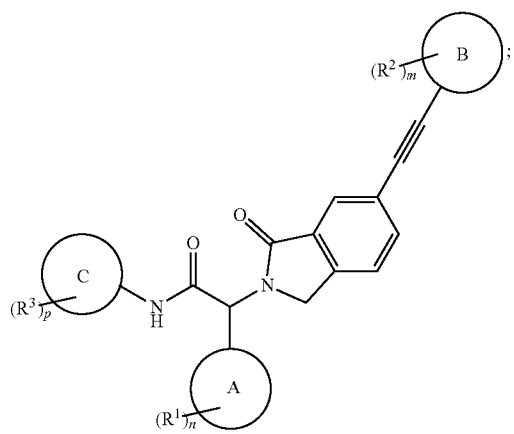

or a pharmaceutically acceptable salt thereof.

21 Claims, No Drawings

SUBSTITUTED ISOINDOLE ALLOSTERIC EGFR INHIBITORS

CROSS-REFERENCE TO RELATED APPLICATIONS

This application is a continuation of International Application No. PCT/EP2018/064399, filed in the International Patent Cooperation Treaty, European Receiving Office on Jun. 1, 2018, which claims the benefit of European Patent Application No. 17174334.7, filed Jun. 2, 2017, U.S. Provisional Application No. 62/514,244, filed Jun. 2, 2017, and U.S. Provisional Application No. 62/543,438, filed Aug. 10, 2017. The entirety of these applications are hereby incorporated by reference herein for all purposes.

FIELD OF THE INVENTION

The present invention provides compounds which are selective allosteric inhibitors of TMLR, TMLRCS, LR, LRCS containing EGFR mutants, their manufacture, pharmaceutical compositions containing them and their use as therapeutically active substances.

BACKGROUND OF THE INVENTION

The HER family receptor tyrosine kinases are mediators of cell growth, differentiation and survival. The receptor family includes four distinct members, i.e. epidermal growth factor receptor (EGFR, ErbB1, or HER1) HER2 (ErbB2), HER3 (ErbB3) and HER4 (ErbB4). Upon ligand binding the receptors form homo and heterodimers and subsequent activation of the intrinsic tyrosine kinase activity leads to receptor auto-phosphorylation and the activation of downstream signaling molecules (Yarden et al.[1]). De-regulation of EGFR by overexpression or mutation has been implicated in many types of human cancer including colorectal, pancreatic, gliomas, head and neck and lung cancer, in particular non-small cell lung cancer (NSCLC) and several EGFR targeting agents have been developed over the years (Ciardiello et al.[2]). Erlotinib (Tarceva®), a reversible inhibitor of the EGFR tyrosine kinase was approved in numerous countries for the treatment of recurrent NSCLC.

An impressive single agent activity of EGFR tyrosine kinase inhibitors is observed in a subset of NSCLC patients whose tumors harbor somatic kinase domain mutations, whereas clinical benefit in wild-type EGFR patients is greatly diminished (Paez et al.[3]). The most common somatic mutations of EGFR are exon 19 deletions with delta 746-750 the most prevalent mutation and the exon 21 amino acid substitutions with L858R the most frequent mutation (Sharma et al.[4]).

Treatment resistance arises frequently, often due to the secondary T790M mutation within the ATP site of the receptor. Some developed mutant-selective irreversible inhibitors are highly active against the T790M mutant, but their efficacy can be compromised by acquired mutation of C797S, that is the cysteine residue with which they form a key covalent bond (Thress et al[5].). C797S mutation was further reported by Wang to be a major mechanism for resistance to T790M-targeting EGFR inhibitors (Wang et al.[6]). Additional mutations that cause resistance to Osimertinib are described by Yang, for example L718Q.(Yang et al[7].)

As most available EGFR tyrosine kinase inhibitors target the ATP-site of the kinase, there is a need for new therapeutic agents that work differently, for example through targeting drug-resistant EGFR mutants. The wild-type receptor, however, maintains untroubled.

Recent studies suggest that purposefully targeting allosteric sites might lead to mutant-selective inhibitors (Jia et al [8].)

There is just a need in the generation of selective molecules that specifically inhibit TMLR, TMLRCS, LRCS containing EGFR mutants useful for the therapeutic and/or prophylactic treatment of cancer, in particular T790M and C797S containing EGFR mutants.

WO2009158369[9] describes certain heterocyclic antibacterial agents. WO2016183534[10] describes certain heterocyclic compounds suitable as EBNA1 inhibitors. WO2011128279 describes certain heterocyclic compounds suitable as mGluR5 modulators.

SUMMARY OF THE INVENTION

The present invention provides an isoindoline-acetylene of formula I, or a pharmaceutically acceptable salt thereof,

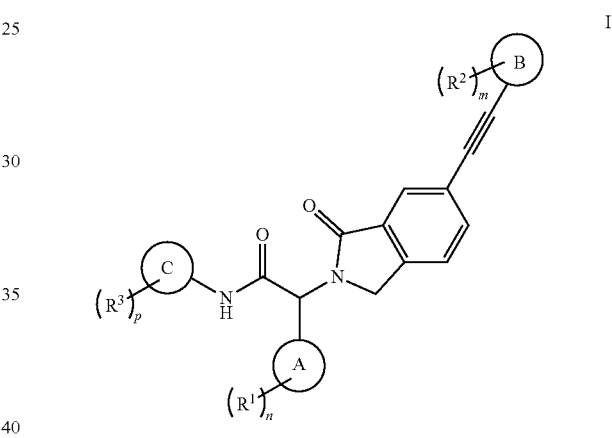

wherein the substituents and variables are as described below and in the claims, or a pharmaceutically acceptable salt thereof.

The present compounds are useful for the therapeutic and/or prophylactic treatment of cancer.

DETAILED DESCRIPTION OF THE INVENTION

The present invention provides a compound of formula I and their pharmaceutically acceptable salts thereof, the preparation of the above-mentioned compounds, medicaments containing them and their manufacture as well as the use of the above-mentioned compounds in the therapeutic and/or prophylactic treatment of cancer, in particular non-small-cell lung cancer.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methyl-propyl), 1,2-dimethyl-propyl and the like. A specific group is methyl.

The term "halogen-$C_{1-6}$-alkyl", alone or in combination with other groups, refers to $C_{1-6}$-alkyl as defined herein, which is substituted by one or multiple halogen, particularly 1-5 halogen, more particularly 1-3 halogen. Particular halogen is fluoro. Particular "halogen-$C_{1-6}$-alkyl" is fluoro-$C_{1-6}$-alkyl and a particular "halogen-$C_{1-3}$-alkyl" is fluoro-$C_{1-3}$-alkyl. Examples are trifluoromethyl, difluoromethyl, fluoromethyl and the like.

The term "cyano", alone or in combination with other groups, refers to N≡C—(NC—).

The term "amino", alone or in combination with other groups, refers to $NH_2$.

The term "hydroxy", alone or in combination with other groups, refers to OH.

The term "halogen", alone or in combination with other groups, denotes chloro (Cl), iodo (I), fluoro (F) and bromo (Br). A specific group is F.

The term "heteroaryl", alone or in combination with other groups, refers to an aromatic carbocyclic group of having a single 4 to 8 membered ring, in particular 5 to 8, or multiple condensed rings comprising 6 to 14, in particular 6 to 10 ring atoms and containing 1, 2 or 3 heteroatoms individually selected from N, O and S, in particular 1N or 2N, in which group at least one heterocyclic ring is aromatic. The term "5-membered heteroaryl" refers to a single 5-membered aromatic ring, containing 1 or 2 heteroatoms selected from N, O and S, in particular one N and one S, for example thiazolyl. A specific group is thiazol-2-yl. The term "6-membered heteroaryl" refers to a single 6-membered aromatic ring, containing 1 or 2 heteroatoms selected from N, O and S, in particular one N, for example pyridinyl. A specific group is 2-pyridyl. Examples of "heteroaryl" include benzofuryl, benzoimidazolyl, 1H-benzoimidazolyl, benzoxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Specific groups are pyridinyl and thiazolyl.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. A specific group is methoxy.

The term "halogen-$C_{1-6}$-alkoxy", alone or in combination with other groups, refers to $C_{1-6}$-alkoxy as defined herein, which is substituted by one or multiple halogen, particularly 1-5 halogen, more particularly 1-3 halogen. Particular halogen is fluoro. Particular "halogen-$C_{1-6}$-alkoxy" is fluoro-$C_{1-6}$-alkoxy and a particular "halogen-$C_{1-3}$-alkoxy" is fluoro-$C_{1-3}$-alkoxy. A specific group is —O—$CF_3$.

The term "N-containing heterocyclyl" or "heterocyclyl" refers to a monovalent saturated or partly unsaturated mono- or bicyclic ring system of 4 to 9 ring atoms, comprising 1, 2, or 3 ring heteroatoms that are N, the remaining ring atoms being carbon. Bicyclic means consisting of two cycles having two ring atoms in common, i.e. the bridge separating the two rings is either a single bond or a chain of one or two ring atoms. Examples are pyrrolidinyl, piperidinyl and piperazinyl.

The term "aryl" denotes a monovalent aromatic carbocyclic mono- or bicyclic ring system comprising 6 to 10 carbon ring atoms. Examples of aryl moieties include phenyl and naphthyl. Specific "aryl" is phenyl.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "a pharmaceutically acceptable salt" refers to a salt that is suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. Specific acids are hydrochloric acid, trifluoroacetic acid and fumaric acid.

The terms "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant ($K_i$) using the Cheng-Prusoff equation[11].

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments may be combined.

One embodiment of the invention provides a compound of formula I,

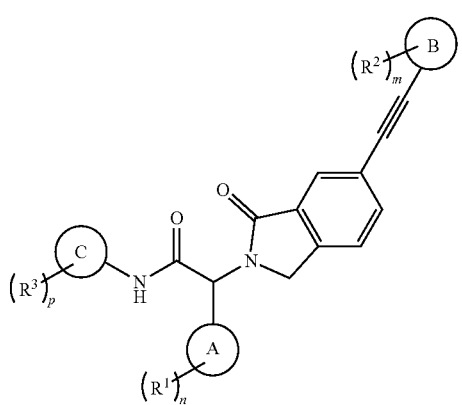

wherein
A is aryl or heteroaryl,
B is aryl or heteroaryl,
C is heteroaryl,
$R^1$ is each independently selected from the group consisting of
   i) amino,
   ii) $C_{1-6}$-alkyl,
   iii) $C_{1-6}$-alkoxy,
   iv) cyano,
   v) halogen,
   vi) halogen-$C_{1-6}$-alkyl,
   vii) halogen-$C_{1-6}$-alkoxy, and
   viii) hydroxy;
$R^2$ is each independently selected from the group consisting of
   i) —(CH$_2$)$_k$—N(R$^4$,R$^5$),
   ii) —(C=O)—N(R$^4$,R$^5$),
   iii) halogen,
   iv) —NH—(C=O)—$C_{1-6}$-alkyl, and
   v) $C_{1-6}$-alkyl;
$R^3$ is each independently selected from the group consisting of
   i) amino,
   ii) $C_{1-6}$-alkyl,
   iii) $C_{1-6}$-alkoxy,
   iv) cyano,
   v) halogen,
   vi) halogen-$C_{1-6}$-alkyl,
   vii) halogen-$C_{1-6}$-alkoxy, and
   viii) hydroxy;
$R^4$ is each independently selected from the group consisting of
   i) H, and
   ii) $C_{1-6}$-alkyl;
$R^5$ is each independently selected from the group consisting of
   i) H,
   ii) $C_{1-6}$-alkyl, and
   iii) —(C=O)—$C_{1-6}$-alkyl;
or $R^4$ and $R^5$ form together with the N they are attached to a heterocyclyl, which heterocyclyl is optionally be substituted by $R^6$.
$R^6$ is each independently selected from the group consisting of
   i) —OH,
   ii) $C_{1-6}$-alkyl, and
   iii) —(C=O)—$C_{1-6}$-alkyl;
k is 0, 1 or 2,
n is 0, 1, 2 or 3;
m is 0, 1 or 2
p is 0 or 1;
or a pharmaceutically acceptable salt thereof.

A certain embodiment of the invention relates to the compound of formula I as described herein, or a pharmaceutically acceptable salt thereof, wherein
A is aryl or heteroaryl,
B is aryl or heteroaryl,
C is heteroaryl,
$R^1$ is each independently selected from the group consisting of
   i) amino,
   ii) $C_{1-6}$-alkyl,
   iii) $C_{1-6}$-alkoxy,
   iv) cyano,
   v) halogen,
   vi) halogen-$C_{1-6}$-alkyl,
   vii) halogen-$C_{1-6}$-alkoxy, and
   viii) hydroxy;
$R^2$ is each independently selected from the group consisting of
   i) —(CH$_2$)$_k$—N(R$^4$,R$^5$),
   ii) —(C=O)—N(R$^4$,R$^5$),
   iii) —NH—(C=O)—$C_{1-6}$-alkyl, and
   iv) $C_{1-6}$-alkyl;

$R^3$ is each independently selected from the group consisting of
i) amino,
ii) $C_{1-6}$-alkyl,
iii) $C_{1-6}$-alkoxy,
iv) cyano,
v) halogen,
vi) halogen-$C_{1-6}$-alkyl,
vii) halogen-$C_{1-6}$-alkoxy, and
viii) hydroxy;

$R^4$ is each independently selected from the group consisting of
i) H, and
ii) $C_{1-6}$-alkyl;

$R^5$ is each independently selected from the group consisting of
i) H,
ii) $C_{1-6}$-alkyl, and
iii) —(C=O)—$C_{1-6}$-alkyl;

or $R^4$ and $R^5$ form together with the N they are attached to a heterocyclyl;

k is 0, 1 or 2,
n is 0, 1, 2 or 3;
m is 0, 1 or 2
p is 0 or 1.

A certain embodiment of the invention relates to the compound of formula I as described herein, or a pharmaceutically acceptable salt thereof, wherein A is aryl, in particular phenyl.

A certain embodiment of the invention relates to the compound of formula I as described herein, or a pharmaceutically acceptable salt thereof, wherein A is aryl.

A certain embodiment of the invention relates to the compound of formula I as described herein, or a pharmaceutically acceptable salt thereof, wherein A is phenyl.

A certain embodiment of the invention relates to the compound of formula I as described herein, or a pharmaceutically acceptable salt thereof, wherein A is pyridinyl.

A certain embodiment of the invention relates to the compound of formula I as described herein, or a pharmaceutically acceptable salt thereof, wherein B is aryl, in particular phenyl.

A certain embodiment of the invention relates to the compound of formula I as described herein, or a pharmaceutically acceptable salt thereof, wherein B is aryl.

A certain embodiment of the invention relates to the compound of formula I as described herein, or a pharmaceutically acceptable salt thereof, wherein B is phenyl.

A certain embodiment of the invention relates to the compound of formula I as described herein, or a pharmaceutically acceptable salt thereof, wherein B is heteroaryl, in particular pyridinyl.

A certain embodiment of the invention relates to the compound of formula I as described herein, or a pharmaceutically acceptable salt thereof, wherein B is heteroaryl.

A certain embodiment of the invention relates to the compound of formula I as described herein, or a pharmaceutically acceptable salt thereof, wherein B is pyridinyl.

A certain embodiment of the invention relates to the compound of formula I as described herein, or a pharmaceutically acceptable salt thereof, wherein B is phenyl or pyridinyl.

A certain embodiment of the invention relates to the compound of formula I as described herein, or a pharmaceutically acceptable salt thereof, wherein C is heteroaryl, in particular thiazolyl.

A certain embodiment of the invention relates to the compound of formula I as described herein, or a pharmaceutically acceptable salt thereof, wherein C is heteroaryl.

A certain embodiment of the invention relates to the compound of formula I as described herein, or a pharmaceutically acceptable salt thereof, wherein C is heteroaryl, in particular thiazolyl or pyridinyl.

A certain embodiment of the invention relates to the compound of formula I as described herein, or a pharmaceutically acceptable salt thereof, wherein C is thiazolyl or pyridinyl.

A certain embodiment of the invention relates to the compound of formula I as described herein, or a pharmaceutically acceptable salt thereof, wherein C is pyridinyl.

A certain embodiment of the invention relates to the compound of formula I as described herein, or a pharmaceutically acceptable salt thereof, wherein n is 0, 1 or 2.

A certain embodiment of the invention relates to the compound of formula I as described herein, or a pharmaceutically acceptable salt thereof, wherein n is 0.

A certain embodiment of the invention relates to the compound of formula I as described herein, or a pharmaceutically acceptable salt thereof, wherein n is 1.

A certain embodiment of the invention relates to the compound of formula I as described herein, or a pharmaceutically acceptable salt thereof, wherein n is 2.

A certain embodiment of the invention relates to the compound of formula I as described herein, or a pharmaceutically acceptable salt thereof, wherein m is 1.

A certain embodiment of the invention relates to the compound of formula I as described herein, or a pharmaceutically acceptable salt thereof, wherein m is 0.

A certain embodiment of the invention relates to the compound of formula I as described herein, or a pharmaceutically acceptable salt thereof, wherein p is 0.

A certain embodiment of the invention relates to the compound of formula I as described herein, or a pharmaceutically acceptable salt thereof, wherein p is 1.

A certain embodiment of the invention relates to the compound of formula I as described herein, or a pharmaceutically acceptable salt thereof, wherein $R^1$ is halogen.

A certain embodiment of the invention relates to the compound of formula I as described herein, or a pharmaceutically acceptable salt thereof, wherein $R^1$ is F.

A certain embodiment of the invention relates to the compound of formula I as described herein, or a pharmaceutically acceptable salt thereof, wherein $R^2$ is —(C=O)-morpholinyl, —(C=O)N(H,CH$_3$), —CH$_2$-(4-methylpiperazinyl), —CH$_2$-(4-acetylpiperazinyl), —CH$_2$-(4-ethylpiperazinyl), —CH$_2$-(4-hydroxy-piperidyl), —CH$_2$-(morpholinyl), —CH$_2$NH$_2$, —CH$_2$-piperazinyl, Cl, —N(H, C=OCH$_3$), or —NH$_2$, in particular —C=O-morpholinyl, —(C=O)N(H,CH$_3$), —CH$_2$-(4-acetylpiperazinyl), —CH$_2$-(4-ethylpiperazinyl), —CH$_2$-morpholinyl, —CH$_2$—NH$_2$, —CH$_2$-piperazinyl, —N(H,(C=O)CH$_3$) or —NH$_2$.

A certain embodiment of the invention relates to the compound of formula I as described herein, or a pharmaceutically acceptable salt thereof, wherein $R^2$ is —(C=O)-morpholinyl, —(C=O)N(H,CH$_3$), —CH$_2$-(4-methylpiperazinyl), —CH$_2$-(4-acetylpiperazinyl), —CH$_2$-(4-ethylpiperazinyl), —CH$_2$-(4-hydroxy-piperidyl), —CH$_2$-(morpholinyl), —CH$_2$NH$_2$, —CH$_2$-piperazinyl, Cl, —N(H, C=OCH$_3$), or —NH$_2$.

A certain embodiment of the invention relates to the compound of formula I as described herein, or a pharmaceutically acceptable salt thereof, wherein $R^2$ is —C=O-morpholinyl, —(C=O)N(H,CH$_3$), —CH$_2$-(4-acetylpiperazinyl), —CH₂-(4-ethylpiperazinyl), —CH₂-morpholinyl, —CH₂—NH₂, —CH₂-piperazinyl, —N(H,(C═O)CH₃) or —NH₂.

A certain embodiment of the invention relates to the compound of formula I as described herein, or a pharmaceutically acceptable salt thereof, wherein $R^2$ is —NH₂.

A certain embodiment of the invention relates to the compound of formula I as described herein, or a pharmaceutically acceptable salt thereof, wherein $R^3$ is —NH₂.

A certain embodiment of the invention relates to the compound of formula I as described herein, or a pharmaceutically acceptable salt thereof, wherein A is phenyl, n is 0, B is phenyl, m is 0 and C is thiazolyl.

A certain embodiment of the invention relates to the compound of formula I as described herein, or a pharmaceutically acceptable salt thereof, wherein A is phenyl, n is 0, B is pyridyl, m is 0 and C is thiazolyl.

A certain embodiment of the invention relates to the compound of formula I as described herein, or a pharmaceutically acceptable salt thereof, wherein A is phenyl, n is 1, $R^2$ is —NH₂, B is phenyl, m is 0 and C is thiazolyl.

A certain embodiment of the invention relates to the compound of formula I as described herein, or a pharmaceutically acceptable salt thereof, wherein A is phenyl, n is 1, $R^2$ is —NH₂, B is pyridyl, m is 0 and C is thiazolyl.

A certain embodiment of the invention relates to the compound of formula I as described herein, or a pharmaceutically acceptable salt thereof, that is selected from the group consisting of (2RS)-2-(5-Fluoro-2-hydroxy-phenyl)-2-[1-oxo-6-(2-phenylethynyl)isoindolin-2-yl]-N-thiazol-2-yl-acetamide,
(2RS)-2-(5-Fluoro-2-hydroxy-phenyl)-2-[1-oxo-6-[2-(3-pyridyl)ethynyl]isoindolin-2-yl]-N-thiazol-2-yl-acetamide,
(2RS)-2-(5-Fluoro-2-hydroxy-phenyl)-2-[1-oxo-6-[2-[4-(piperazin-1-ylmethyl)phenyl]ethynyl]isoindolin-2-yl]-N-thiazol-2-yl-acetamide,
(2RS)-2-(5-Fluoro-2-hydroxy-phenyl)-2-[6-[2-[4-(morpholinomethyl)phenyl]ethynyl]-1-oxo-isoindolin-2-yl]-N-thiazol-2-yl-acetamide,
(2RS)-2-(5-Fluoro-2-hy droxy-phenyl)-2-[6-[2-[4-[(4-hydroxy-1-piperidyl)methyl]phenyl]ethynyl]-1-oxo-isoindolin-2-yl]-N-thiazol-2-yl-acetamide,
(2RS)-2-(5-Fluoro-2-hydroxy-phenyl)-2-[6-[2-[4-[(4-methylpiperazin-1-yl)methyl]phenyl]ethynyl]-1-oxo-isoindolin-2-yl]-N-thiazol-2-yl-acetamide,
(2RS)-2-(5-Fluoro-2-hydroxy-phenyl)-2-[7-fluoro-1-oxo-6[-2-(3-pyridyl)ethynyl]isoindolin-2-yl]-N-thiazol-2-yl-acetamide,
(2RS)-2-[1-Oxo-6-(2-phenylethynyl)isoindolin-2-yl]-2-phenyl-N-thiazol-2-yl-acetamide,
(2RS)-2-[1-oxo-6-[2-(3-pyridyl)ethynyl]isoindolin-2-yl]-2-phenyl-N-thiazol-2-yl-acetamide,
(2RS)-2-[1-Oxo-6-[2-[4-(piperazin-1-ylmethyl)phenyl]ethynyl]isoindolin-2-yl]-2-phenyl-N-thiazol-2-yl-acetamide,
(2RS)-2-[6-[2-(2-Aminopyrimidin-5-yl)ethynyl]-1-oxo-isoindolin-2-yl]-2-(5-fluoro-2-hydroxy-phenyl)-N-thiazol-2-yl-acetamide,
(2RS)-2-[6-[2-(2-Chloro-4-pyridyl)ethynyl]-1-oxo-isoindolin-2-yl]-2-(5-fluoro-2-hydroxy-phenyl)-N-thiazol-2-yl-acetamide,
(2RS)-2-[6-[2-(6-Acetamido-3-pyridyl)ethynyl]-1-oxo-isoindolin-2-yl]-2-phenyl-N-thiazol-2-yl-acetamide,
(2RS)-2-[6-[2-(6-Amino-3-pyridypethynyl]-1-oxo-isoindolin-2-yl]-2-phenyl-N-thiazol-2-yl-acetamide,
(2RS)-2-[6-[2-(6-Amino-3-pyridyl)ethynyl]-1-oxo-isoindolin-2-yl]-2-(3-fluorophenyl)-N-thiazol-2-yl-acetamide,
(2RS)-2-[6-[2-(6-Amino-3-pyridyl)ethynyl]-1-oxo-isoindolin-2-yl]-2-(2,5-difluorophenyl)-N-thiazol-2-yl-acetamide,
(2RS)-2-[6-[2-(6-Amino-3-pyridyl)ethynyl]-1-oxo-isoindolin-2-yl]-2-(1,4,5,6-tetrahydrocyclopenta[c]pyrazol-3-yl)-N-thiazol-2-yl-acetamide,
(2RS)-2-[6-[2-(6-Amino-3-pyridyl)ethynyl]-1-oxo-isoindolin-2-yl]-2-(5-fluoro-2-hydroxy-phenyl)-N-thiazol-2-yl-acetamide,
(2RS)-2-[6-[2-(6-Amino-3-pyridyl)ethynyl]-1-oxo-isoindolin-2-yl]-2-(5-fluoro-2-hydroxy-phenyl)-N-(2-pyridyl)acetamide,
(2RS)-2-[6-[2-(6-Amino-3-pyridyl)ethynyl]-1-oxo-isoindolin-2-yl]-2-(5-chloro-2-hydroxy-phenyl)-N-thiazol-2-yl-acetamide,
(2RS)-2-[6-[2-(6-Amino-3-pyridyl)ethynyl]-1-oxo-isoindolin-2-yl]-2-(2-hydroxyphenyl)-N-thiazol-2-yl-acetamide,
(2RS)-2-[6-[2-(6-Amino-3-pyridypethynyl]-1-oxo-isoindolin-2-yl]-2-(3-hydroxy-2-pyridyl)-N-thiazol-2-yl-acetamide trifluoroacetate,
(2RS)-2-[6-[2-(6-Amino-3-pyridyl)ethynyl]-7-methyl-1-oxo-isoindolin-2-yl]-2-(5-fluoro-2-hydroxy-phenyl)-N-thiazol-2-yl-acetamide,
(2RS)-2-[6-[2-(6-Amino-3-pyridyl)ethynyl]-7-methyl-1-oxo-isoindolin-2-yl]-2-(5-fluoro-2-hydroxy-phenyl)-N-(2-pyridyl)acetamide,
(2RS)-2-[6-[2-[4-(Aminomethyl)phenyl]ethynyl]-1-oxo-isoindolin-2-yl]-2-phenyl-N-thiazol-2-yl-acetamide,
(2RS)-2-[6-[2-[4-(Morpholinomethyl)phenyl]ethynyl]-1-oxo-isoindolin-2-yl]-2-phenyl-N-thiazol-2-yl-acetamide,
(2RS)-2-[6-[2-[4-[(4-acetylpiperazin-1-yl)methyl]phenyl]ethynyl]-1-oxo-isoindolin-2-yl]-2-phenyl-N-thiazol-2-yl-acetamide,
(2RS)-2-[6-[2-[4-[(4-Ethylpiperazin-1-yl)methyl]phenyl]ethynyl]-1-oxo-isoindolin-2-yl]-2-phenyl-N-thiazol-2-yl-acetamide,
(2RS)-2-[6-[2-[4-[(4-Ethylpiperazin-1-yl)methyl]phenyl]ethynyl]-1-oxo-isoindolin-2-yl]-2-(5-fluoro-2-hydroxy-phenyl)-N-thiazol-2-yl-acetamide,
(2RS)-2-[6-[2-[6-(Morpholine-4-carbonyl)-3-pyridyl]ethynyl]-1-oxo-isoindolin-2-yl]-2-phenyl-N-thiazol-2-yl-acetamide, and
N-Methyl-5-[2-[3-oxo-2-[(1RS)-2-oxo-1-phenyl-2-(thiazol-2-ylamino)ethyl]isoindolin-5-yl]ethynyl]pyridine-2-carboxamide.

A certain embodiment of the invention relates to the compound of formula I as described herein, or a pharmaceutically acceptable salt thereof, that is selected from the group consisting of
(2RS)-2-[1-Oxo-6-(2-phenylethynyl)isoindolin-2-yl]-2-phenyl-N-thiazol-2-yl-acetamide,
(2RS)-2-[1-oxo-6-[2-(3-pyridyl)ethynyl]isoindolin-2-yl]-2-phenyl-N-thiazol-2-yl-acetamide,
(2RS)-2-[1-Oxo-6-[2-[4-(piperazin-1-ylmethyl)phenyl]ethynyl]isoindolin-2-yl]-2-phenyl-N-thiazol-2-yl-acetamide,
(2RS)-2-[6-[2-(6-Acetamido-3-pyridyl)ethynyl]-1-oxo-isoindolin-2-yl]-2-phenyl-N-thiazol-2-yl-acetamide,
(2RS)-2-[6-[2-(6-Amino-3-pyridypethynyl]-1-oxo-isoindolin-2-yl]-2-phenyl-N-thiazol-2-yl-acetamide,
(2RS)-2-[6-[2-(6-Amino-3-pyridyl)ethynyl]-1-oxo-isoindolin-2-yl]-2-(3-fluorophenyl)-N-thiazol-2-yl-acetamide,
(2RS)-2-[6-[2-(6-Amino-3-pyridyl)ethynyl]-1-oxo-isoindolin-2-yl]-2-(2,5-difluorophenyl)-N-thiazol-2-yl-acetamide,
(2RS)-2-[6-[2-(6-Amino-3-pyridyl)ethynyl]-1-oxo-isoindolin-2-yl]-2-(1,4,5,6-tetrahydrocyclopenta[c]pyrazol-3-yl)-N-thiazol-2-yl-acetamide, (2RS)-2-[6-[2-[4-(Aminomethyl)phenyl]ethynyl]-1-oxo-isoindolin-2-yl]-2-phenyl-N-thiazol-2-yl-acetamide,
(2RS)-2-[6-[2[4-(Morpholinomethyl)phenyl]ethynyl]-1-oxo-isoindolin-2-yl]-2-phenyl-N-thiazol-2-yl-acetamide,
(2RS)-2-[6-[2-[4-[(4-acetylpiperazin-1-yl)methyl]phenyl]ethynyl]-1-oxo-isoindolin-2-yl]-2-phenyl-N-thiazol-2-yl-acetamide,
(2RS)-2-[6-[2-[4-[(4-Ethylpiperazin-1-yl)methyl]phenyl]ethynyl]-1-oxo-isoindolin-2-yl]-2-phenyl-N-thiazol-2-yl-acetamide,
(2RS)-2-[6-[2-[6-(Morpholine-4-carbonyl)-3-pyridyl]ethynyl]-1-oxo-isoindolin-2-yl]-2-phenyl-N-thiazol-2-yl-acetamide,
N-Methyl-5-[2-[3-oxo-2-[(1RS)-2-oxo-1-phenyl-2-(thiazol-2-ylamino)ethyl]isoindolin-5-yl]ethynyl]pyridine-2-carboxamide, and
(2RS)-2-[6-[2-(6-Amino-3-pyridyl)ethynyl]-1-oxo-isoindolin-2-yl]-2-(5-fluoro-2-hydroxy-phenyl)-N-thiazol-2-yl-acetamide.

A certain embodiment of the invention relates to the compound of formula I as described herein, or a pharmaceutically acceptable salt thereof, that is selected from the group consisting of
(2RS)-2-[1-Oxo-6-(2-phenylethynyl)isoindolin-2-yl]-2-phenyl-N-thiazol-2-yl-acetamide,
(2RS)-2-[1-oxo-6-[2-(3-pyridyl)ethynyl]isoindolin-2-yl]-2-phenyl-N-thiazol-2-yl-acetamide,
(2RS)-2-[1-Oxo-6-[2-[4-(piperazin-1-ylmethyl)phenyl]ethynyl]isoindolin-2-yl]-2-phenyl-N-thiazol-2-yl-acetamide,
(2RS)-24-[4-[2-(6-Acetamido-3-pyridyl)ethynyl]-1-oxo-isoindolin-2-yl]-2-phenyl-N-thiazol-2-yl-acetamide,
(2RS)-2-[6-[2-(6-Amino-3-pyridypethynyl]-1-oxo-isoindolin-2-yl]-2-phenyl-N-thiazol-2-yl-acetamide,
(2RS)-2-[6[2-(6-Amino-3-pyridyl)ethynyl]-1-oxo-isoindolin-2-yl]-2-(3-fluorophenyl)-N-thiazol-2-yl-acetamide,
(2RS)-2-[6[42-(6-Amino-3-pyridyl)ethynyl]-1-oxo-isoindolin-2-yl]-2-(2,5-difluorophenyl)-N-thiazol-2-yl-acetamide,
(2RS)-2-[6-[2-(6-Amino-3-pyridyl)ethynyl]-1-oxo-isoindolin-2-yl]-2-(1,4,5,6-tetrahydrocyclopenta[c]pyrazol-3-yl)-N-thiazol-2-yl-acetamide,
(2RS)-2-[6-[2-[4-(Aminomethyl)phenyl]ethynyl]-1-oxo-i soindolin-2-yl]-2-phenyl-N-thiazol-2-yl-acetamide,
(2RS)-2-[6-[2-[4-(Morpholinomethyl)phenyl]ethynyl]-1-oxo-i soindolin-2-yl]-2-phenyl-N-thiazol-2-yl-acetami de,
(2RS)-2-[6-[2-[4-[(4-acetylpiperazin-1-yl)methyl]phenyl]ethynyl]-1-oxo-isoindolin-2-yl]-2-phenyl-N-thiazol-2-yl-acetamide,
(2RS)-2-[6-[2-[4-[(4-Ethylpiperazin-1-yl)methyl]phenyl]ethynyl]-1-oxo-isoindolin-2-yl]-2-phenyl-N-thiazol-2-yl-acetamide,
(2RS)-2-[6-[2-[6-(Morpholine-4-carb onyl)-3 -pyridyl]ethynyl]-1-oxo-isoindolin-2-yl]-2-phenyl-N-thiazol-2-yl-acetamide, and
N-Methyl-5-[2-[3-oxo-2-[(1RS)-2-oxo-1-phenyl-2-(thiazol-2-ylamino)ethyl]isoindolin-5-yl]ethynyl]pyridine-2-carb oxamide.

A certain embodiment of the invention relates to the compound of formula I as described herein, or a pharmaceutically acceptable salt thereof, for use as therapeutically active substance.

A certain embodiment of the invention relates to the compound of formula I as described herein, or a pharmaceutically acceptable salt thereof, for the use in the therapeutic and/or prophylactic treatment of cancer, in particular non-small-cell lung cancer.

A certain embodiment of the invention relates to the compound of formula I as described herein, or a pharmaceutically acceptable salt thereof, for the use in the therapeutic and/or prophylactic treatment of non-small-cell lung cancer.

A certain embodiment of the invention relates to the compound of formula I as described herein, or a pharmaceutically acceptable salt thereof, for the manufacture of a medicament for the therapeutic and/or prophylactic treatment of cancer, in particular non-small-cell lung cancer.

A certain embodiment of the invention relates to a pharmaceutical composition comprising the compound of formula I as described herein, or a pharmaceutically acceptable salt thereof, and a pharmaceutically acceptable auxiliary substance.

A certain embodiment of the invention relates to a method for the therapeutic and/or prophylactic treatment of cancer, in particular non-small-cell lung cancer by administering the compound of formula I as described herein, or a pharmaceutically acceptable salt thereof, to a patient.

A certain embodiment of the invention relates to the compound of formula I as described herein, or a pharmaceutically acceptable salt thereof, for the use as a medicament in therapeutic and/or prophylactic treatment of a patient with EGFR activating mutations suffering from cancer, in particular non-small-cell lung cancer, comprising determining the EGFR activating mutations status in said patient and then administering the compound of formula I as described herein, or a pharmaceutically acceptable salt thereof, to said patient.

A certain embodiment of the invention relates to the compound of formula I as described herein, or a pharmaceutically acceptable salt thereof, for the use as a medicament in therapeutic and/or prophylactic treatment of a patient with EGFR activating mutations as determined with a cobas® EGFR Mutation Test v2 suffering from cancer, in particular non-small-cell lung cancer, comprising determining the EGFR activating mutations status in said patient and then administering the compound of formula I as described herein, or a pharmaceutically acceptable salt thereof, to said patient.

Furthermore, the invention includes all optical isomers, i.e. diastereoisomers, diastereomeric mixtures, racemic mixtures, all their corresponding enantiomers and/or tautomers as well as their solvates of the compounds of formula I.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The compounds of formula I may be prepared in accordance with the schemes described in the examples. The starting material is commercially available or may be prepared in accordance with known methods.

The preparation of compounds of formula I is further described in more detail in scheme 1 and in the examples.

An isoindoline-acetylene based compound of general formula I can be obtained for example by amide coupling with an appropriately substituted acid of formula 1 and an appropriately substituted amine of formula 2 with a coupling agent such as TBTU to yield the desired amide derivatives of formula 3. Deprotection followed by ring cyclization with a iodo or bromo methyl 2-(bromomethyl)benzoate of formula 5 yields the desired isoindoline 6. Sonogashira coupling with an appropiate substituted acetylene of formula 7 forms the desired isoindoline-acetylene based compound of general formula I (scheme 1).

Generally speaking, the sequence of steps used to synthesize the compounds of formula I can also be modified in certain cases.

Generally speaking, the sequence of steps used to synthesize the compounds of formula I can also be modified in certain cases.

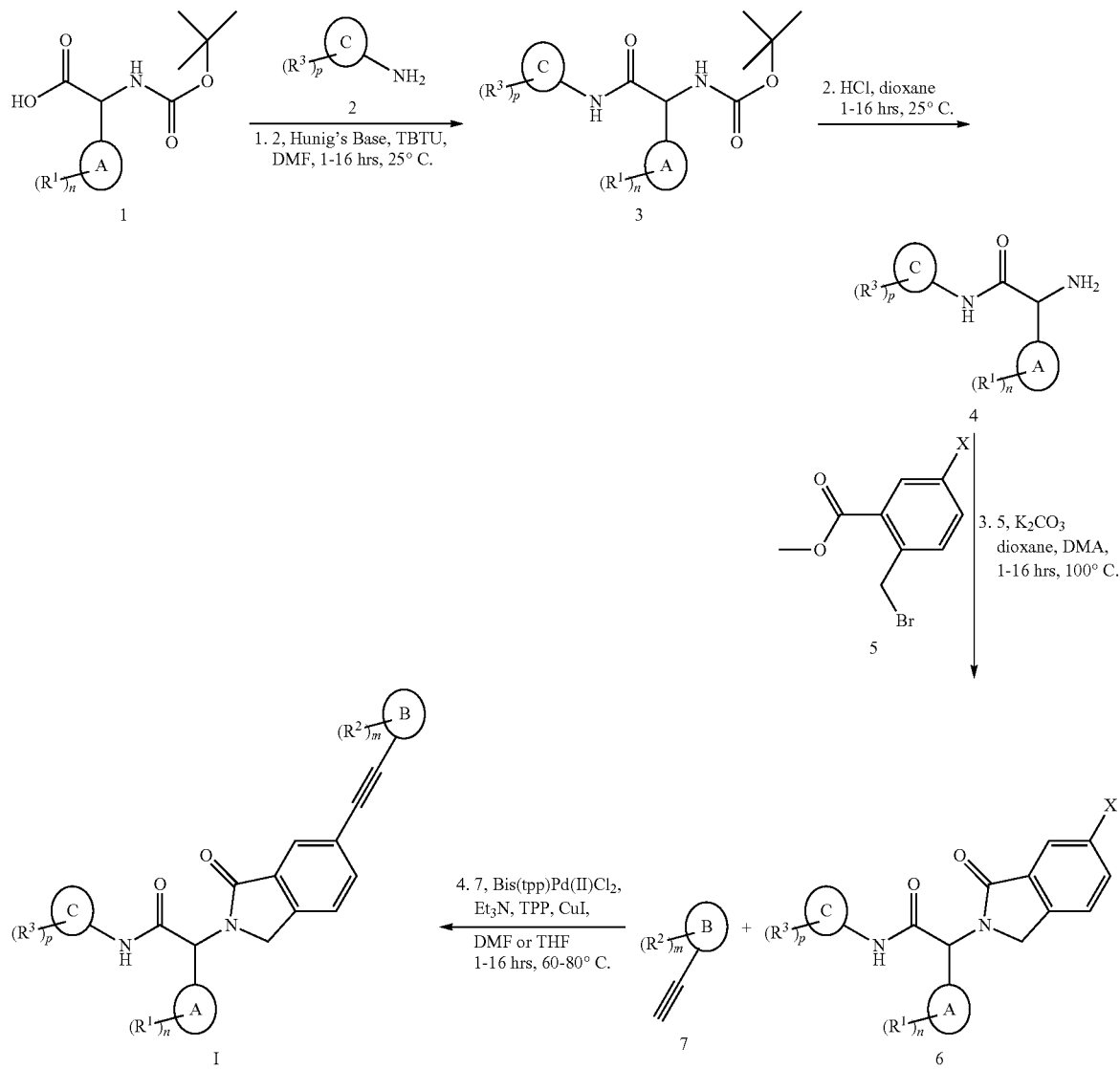

The corresponding pharmaceutically acceptable salts with acids can be obtained by standard methods known to the person skilled in the art, e.g. by dissolving the compound of formula I in a suitable solvent such as e.g. dioxane or tetrahydrofuran and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. M(OH)$_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention may be derivatised at functional groups to provide derivatives which are capable of conversion back to the parent compound in vivo.

Pharmacological Tests

The compounds of formula I and their pharmaceutically acceptable salts possess valuable pharmacological properties. The compounds were investigated in accordance with the test given hereinafter.

HTRF Phospo EGFR Assay (Cellular)

Cell Line and Media

H1975 cell line was obtained from American Type Culture Collection (Manassas, Va., USA). Cells were maintained at 37° C., 5% $CO_2$ in complete Media RPMI 1640 without phenol red containing 0.3 mg/ml glutamine, 100 IU/ml penicillin, and 100 mg/ml streptomycin (Gibco) supplemented with 10% fetal bovine serum (FBS) (Gibco). Compounds were diluted into starving medium RPMI 1640 Media without phenol red containing 0.3 mg/ml glutamine, 100 IU/ml penicillin, and 100 mg/ml streptomycin (Gibco).

Protocol

Cells were cultured overnight in a 384-well white plate (8000 cells/well) using 8 µl of complete medium/well. Cells were washed two times with 20 µl of starving medium. Media was removed by tapping plates on tissue and subsequently 8 µl of fresh starving medium/well was added. Then 4 µl/well of the 3×compound solution, containing a half-log dilution series of the compound or DMSO in starving medium, were added to the cells. After 6 hours at 37° C., 5% $CO_2$ cells were lysed by adding to the compound mix 4 µl/well of the supplemented lysis buffer, followed by incubation for 30 min at room temperature with shaking. Lysates were stored at −20° C. overnight. The following day plates were thawed and 2 µl of anti-Phospho-EGFR Cryptate and 2 µl of anti-Phospho-EGFR-d2 antibody solutions prepared in the detection buffer were added. The plates were then incubated for at least 4 h at room temperature before reading the fluorescence emission at 620 and 665 nm using PHERAstar FX plate reader (BMG Labtech).

TABLE 1

| | IC$_{50}$ value | |
|---|---|---|
| Exam. | Structure | IC$_{50}$ [nM] |
| 1 | 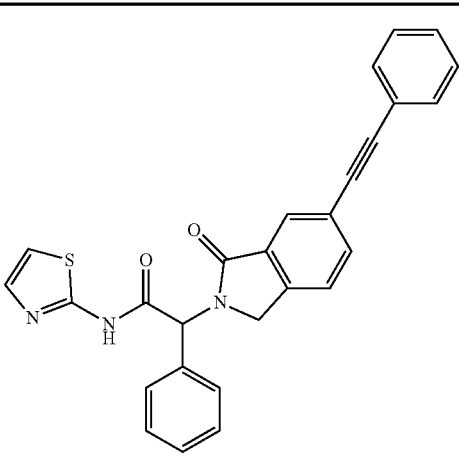 | 45 nM (H1975) |

TABLE 1-continued

| | IC$_{50}$ value | |
|---|---|---|
| Exam. | Structure | IC$_{50}$ [nM] |
| 2 | (structure) | 42 nM (H1975) |
| 3 | (structure) | 32 nM (H1975) |
| 4 | (structure) | 9 nM (H1975) |

TABLE 1-continued
| Exam. | Structure | IC$_{50}$ [nM] |
|---|---|---|
| 5 | 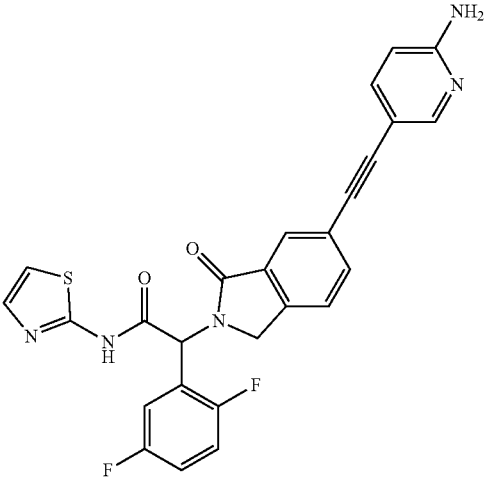 [SMILES: Nc1ccc(C#Cc2ccc3c(c2)C(=O)N(C(C(=O)Nc2nccs2)c2cc(F)ccc2F)C3)cn1] | 7 nM (H1975) |
| 6 | 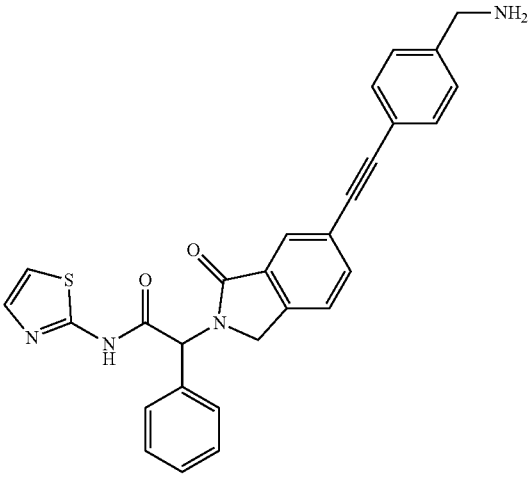 [SMILES: NCc1ccc(C#Cc2ccc3c(c2)C(=O)N(C(C(=O)Nc2nccs2)c2ccccc2)C3)cc1] | 35 nM (H1975) |
| 7 | 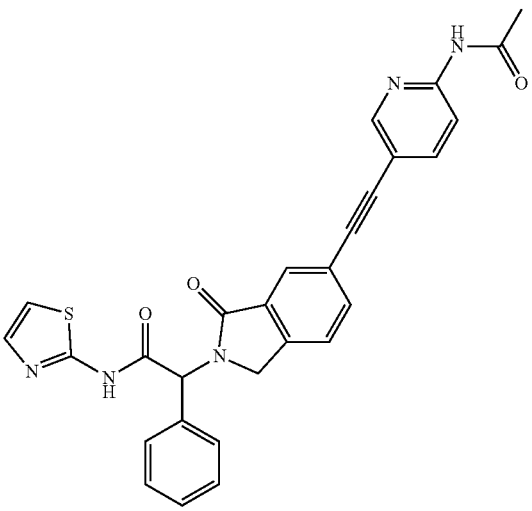 [SMILES: CC(=O)Nc1ccc(C#Cc2ccc3c(c2)C(=O)N(C(C(=O)Nc2nccs2)c2ccccc2)C3)cn1] | 10 nM (H1975) |

TABLE 1-continued
| Exam. | Structure | IC$_{50}$ [nM] |
|---|---|---|
| 8 | 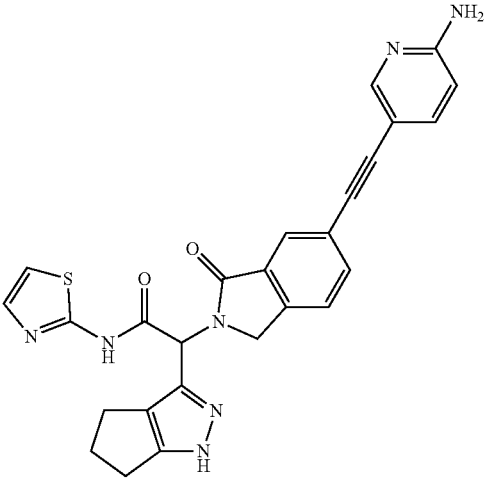 [SMILES: Nc1ccc(C#Cc2ccc3c(c2)C(=O)N(C(C(=O)Nc2nccs2)c2n[nH]c4c2CCC4)C3)cn1] | 1.9 nM (H1975) |
| 9 | 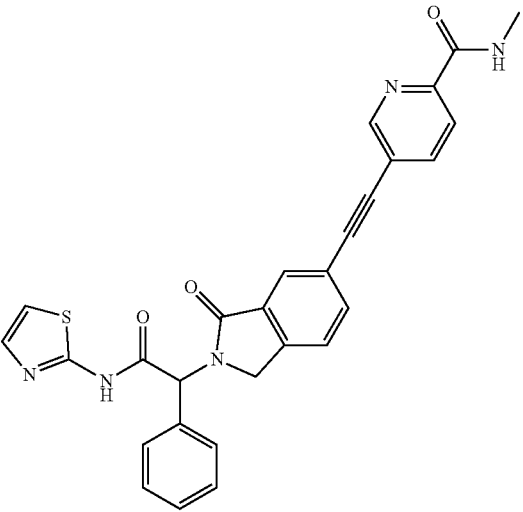 [SMILES: CNC(=O)c1ccc(C#Cc2ccc3c(c2)C(=O)N(C(C(=O)Nc2nccs2)c2ccccc2)C3)cn1] | 16 nM (H1975) |
| 10 | 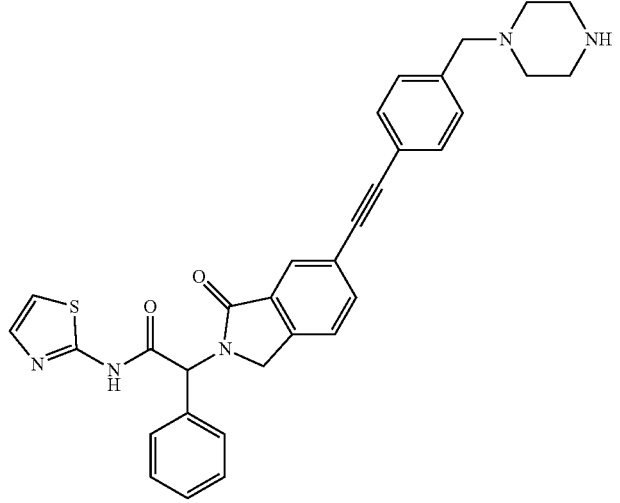 [SMILES: O=C(Nc1nccs1)C(c1ccccc1)N1Cc2ccc(C#Cc3ccc(CN4CCNCC4)cc3)cc2C1=O] | 43 nM (H1975) |

TABLE 1-continued

| Exam. | Structure | IC$_{50}$ [nM] |
|---|---|---|
| 11 | 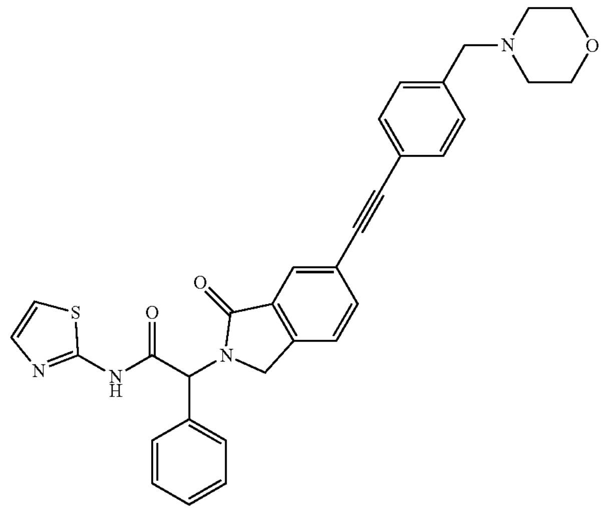 [SMILES: O=C(Nc1nccs1)C(c1ccccc1)N1Cc2ccc(C#Cc3ccc(CN4CCOCC4)cc3)cc2C1=O] | 61 nM (H1975) |
| 12 | 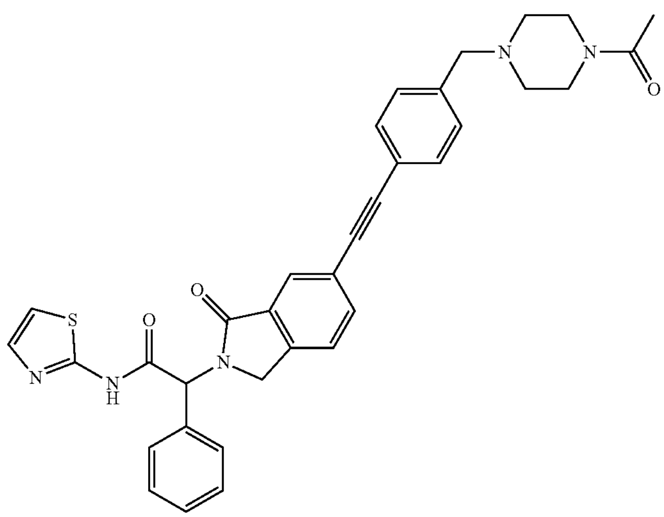 [SMILES: CC(=O)N1CCN(Cc2ccc(C#Cc3ccc4c(c3)C(=O)N(C(C(=O)Nc3nccs3)c3ccccc3)C4)cc2)CC1] | 14 nM (H1975) |
| 13 | 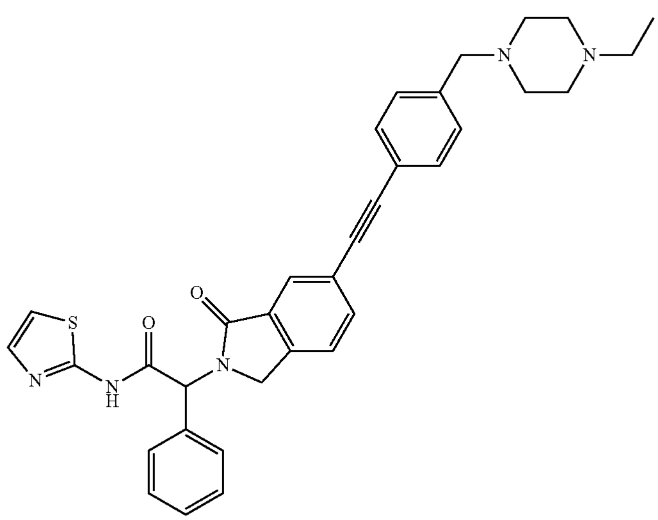 [SMILES: CCN1CCN(Cc2ccc(C#Cc3ccc4c(c3)C(=O)N(C(C(=O)Nc3nccs3)c3ccccc3)C4)cc2)CC1] | 69 nM (H1975) |

TABLE 1-continued

| Exam. | Structure | IC$_{50}$ [nM] |
|---|---|---|
| 14 | 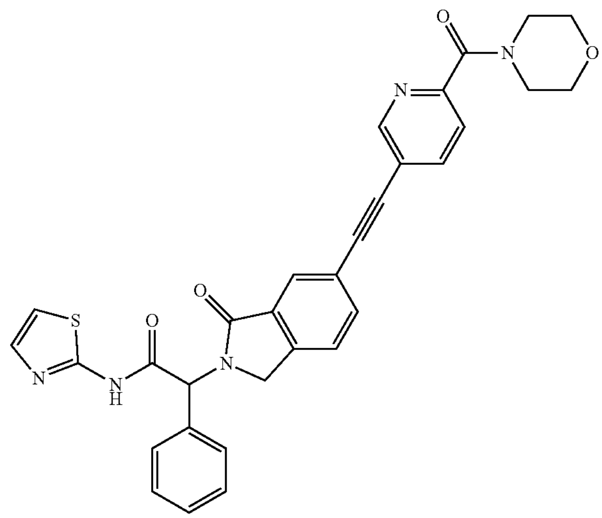 [SMILES: O=C(Nc1nccs1)C(c1ccccc1)N1Cc2ccc(C#Cc3ccc(C(=O)N4CCOCC4)nc3)cc2C1=O] | 51 nM (H1975) |
| 15 | 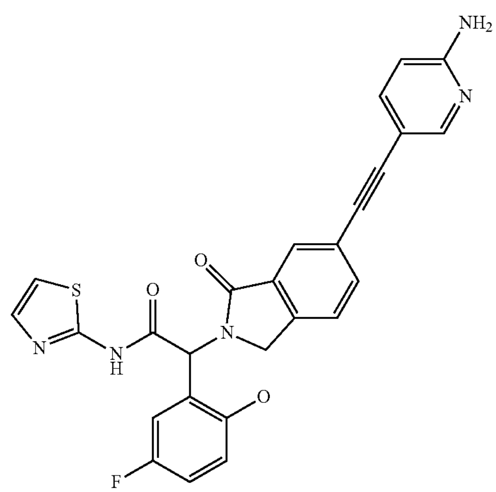 | 1 nM (H1975) |
| 16 | 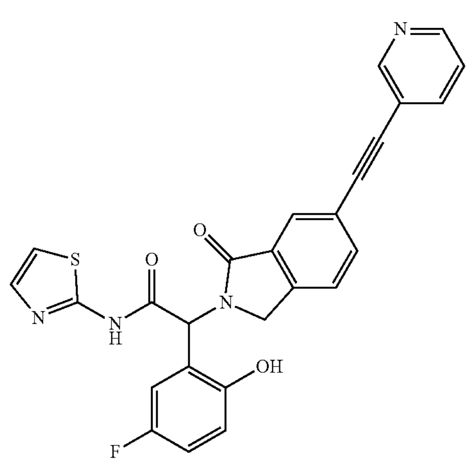 [SMILES: O=C(Nc1nccs1)C(c1cc(F)ccc1O)N1Cc2ccc(C#Cc3cccnc3)cc2C1=O] | 1 nM (H1975) |

TABLE 1-continued

| | | IC$_{50}$ value |
|---|---|---|
| Exam. | Structure | IC$_{50}$ [nM] |
| 17 | | 6 nM (H1975) |
| 18 | | 2 nM (H1975) |
| 19 | | 3 nM (H1975) |

TABLE 1-continued
| Exam. | Structure | IC50 [nM] |
|---|---|---|
| 20 | 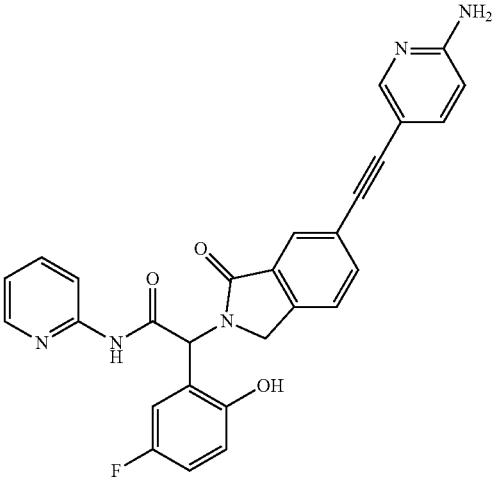 [SMILES: Nc1ccc(C#Cc2ccc3c(c2)C(=O)N(C(C(=O)Nc2ccccn2)c2cc(F)ccc2O)C3)cn1] | 4 nM (H1975) |
| 21 | 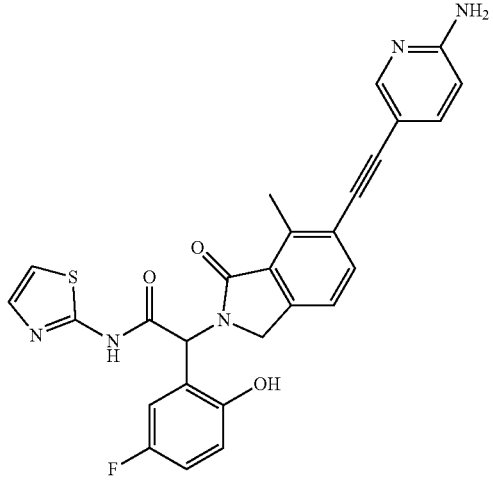 [SMILES: Cc1c(C#Cc2ccc(N)nc2)ccc2c1C(=O)N(C(C(=O)Nc1nccs1)c1cc(F)ccc1O)C2] | 3 nM (H1975) |
| 22 | 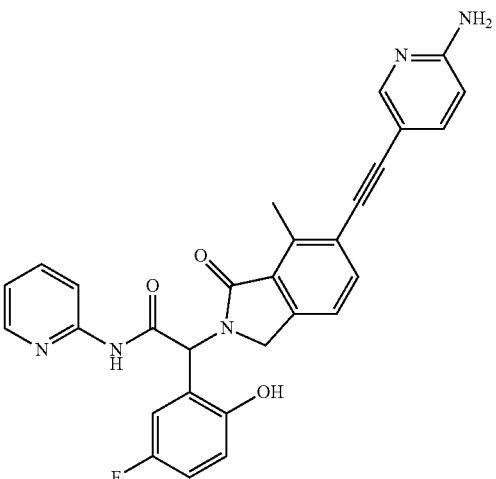 | 3 nM (H1975) |

TABLE 1-continued

| Exam. | Structure | IC$_{50}$ [nM] |
|---|---|---|
| 23 | 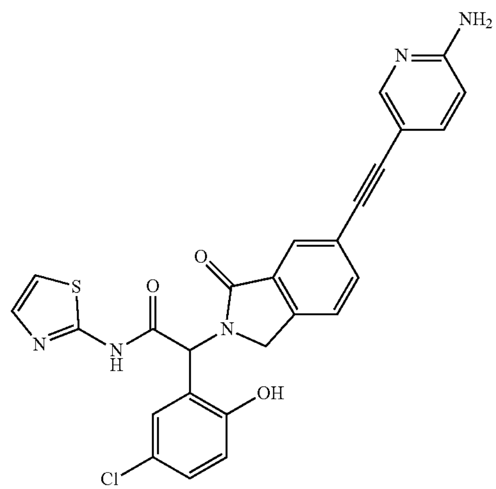 [SMILES: Nc1ccc(C#Cc2ccc3c(c2)C(=O)N(C(C(=O)Nc2nccs2)c2cc(Cl)ccc2O)C3)cn1] | 4 nM (H1975) |
| 24 | 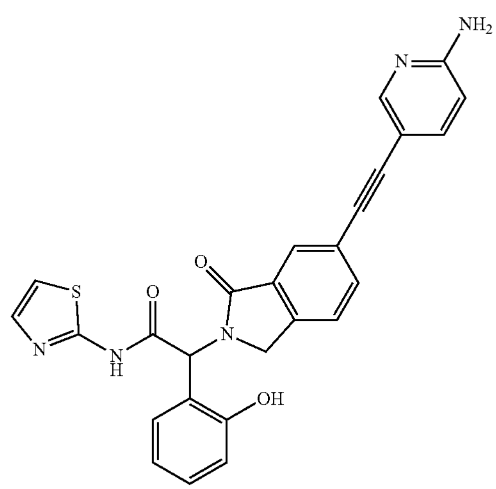 [SMILES: Nc1ccc(C#Cc2ccc3c(c2)C(=O)N(C(C(=O)Nc2nccs2)c2ccccc2O)C3)cn1] | 4 nM (H1975) |
| 25 | 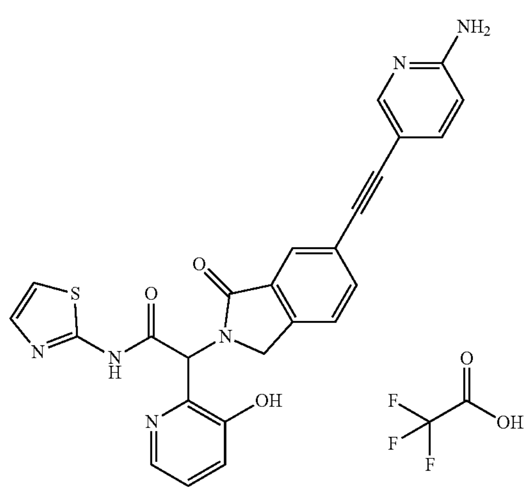 [SMILES: Nc1ccc(C#Cc2ccc3c(c2)C(=O)N(C(C(=O)Nc2nccs2)c2ncccc2O)C3)cn1 ; O=C(O)C(F)(F)F] | 2 nM (H1975) |

TABLE 1-continued
| Exam. | Structure | IC$_{50}$ [nM] |
|---|---|---|
| 26 | 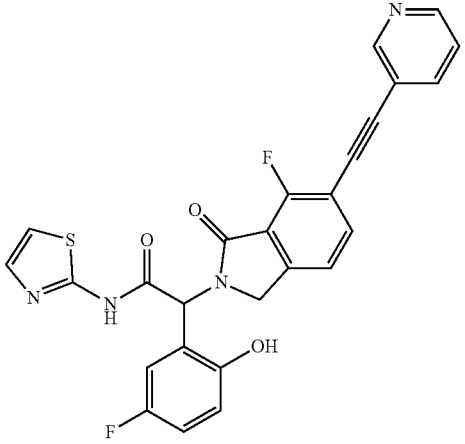 [SMILES: O=C(Nc1nccs1)C(c1cc(F)ccc1O)N1Cc2ccc(C#Cc3cccnc3)c(F)c2C1=O] | 2 nM (H1975) |
| 27 | 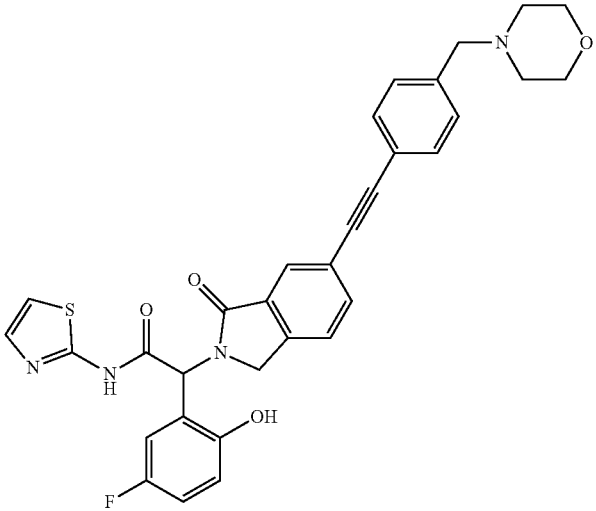 [SMILES: O=C(Nc1nccs1)C(c1cc(F)ccc1O)N1Cc2ccc(C#Cc3ccc(CN4CCOCC4)cc3)cc2C1=O] | 5 nM (H1975) |
| 28 | 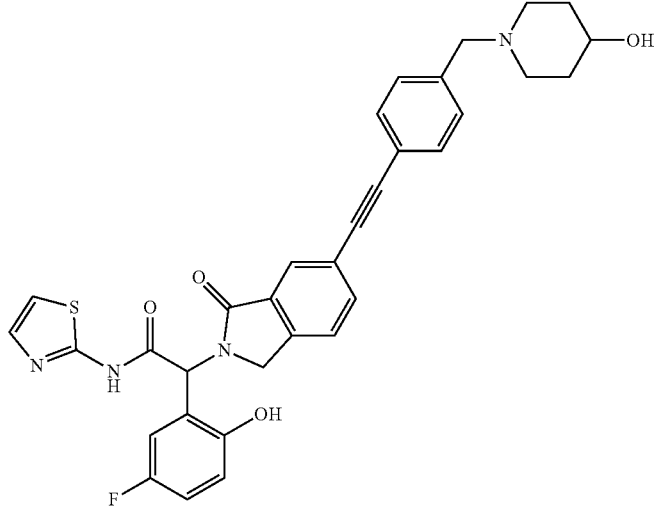 [SMILES: O=C(Nc1nccs1)C(c1cc(F)ccc1O)N1Cc2ccc(C#Cc3ccc(CN4CCC(O)CC4)cc3)cc2C1=O] | 7 nM (H1975) |

TABLE 1-continued

| Exam. | Structure | IC₅₀ [nM] |
|---|---|---|
| 29 | 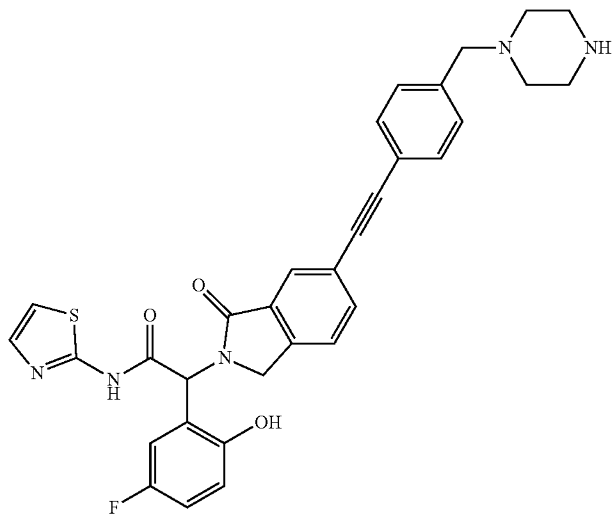 [SMILES: O=C(Nc1nccs1)C(c1cc(F)ccc1O)N1Cc2ccc(C#Cc3ccc(CN4CCNCC4)cc3)cc2C1=O] | 8 nM (H1975) |
| 30 | 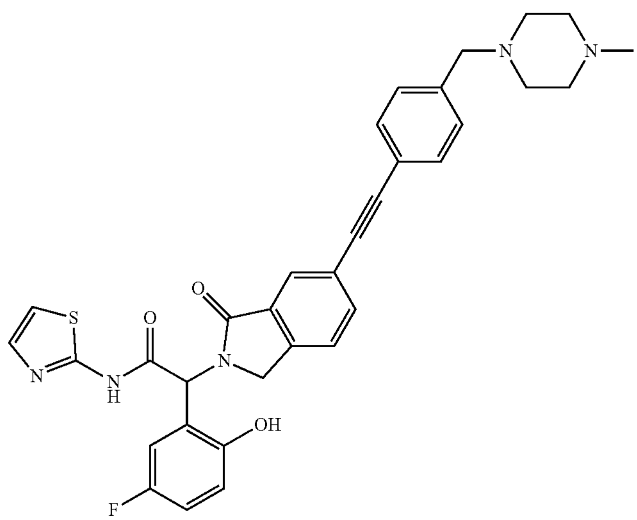 [SMILES: CN1CCN(Cc2ccc(C#Cc3ccc4c(c3)C(=O)N(C(C(=O)Nc3nccs3)c3cc(F)ccc3O)C4)cc2)CC1] | 7 nM (H1975) |
| 31 | 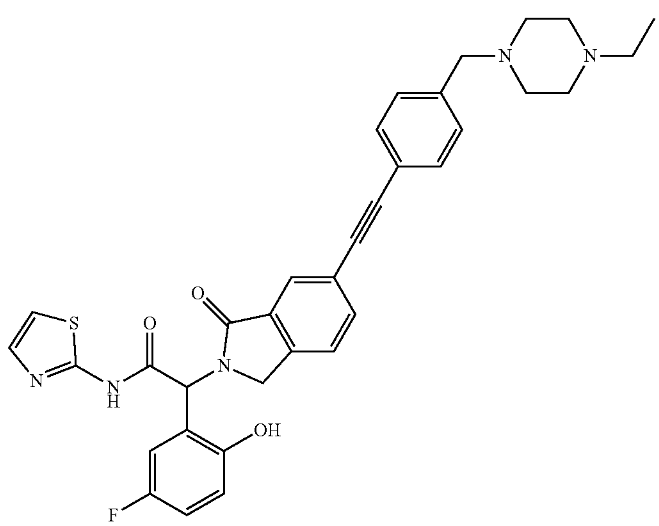 [SMILES: CCN1CCN(Cc2ccc(C#Cc3ccc4c(c3)C(=O)N(C(C(=O)Nc3nccs3)c3cc(F)ccc3O)C4)cc2)CC1] | 7 nM (H1975) |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, drages and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I. Examples of compositions according to the invention are:

Example A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talc | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
| --- | --- |
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6 possible suppository composition

| ingredient | mg/supp. |
| --- | --- |
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7 possible injection solution composition

| ingredient | mg/injection solution. |
| --- | --- |
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8 possible sachet composition

| ingredient | mg/sachet |
| --- | --- |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

Example 1

(2RS)-2-[1-Oxo-6-(2-phenylethynyl)isoindolin-2-yl]-2-phenyl-N-thiazol-2-yl-acetamide Step 1: tert-Butyl N-[(1RS)-2-oxo-1-phenyl-2-(thiazol-2-ylamino)ethyl]carbamate (2RS)-2-(tert-Butoxycarbonylamino)-2-phenyl-acetic acid (9.5 g, 37.8 mmol) was dissolved in 75 ml of ethyl acetate and 10 ml of DMF. Thiazol-2-amine (3.79 g, 37.8 mmol, 1 equiv.), Hunig's base (14.7 g, 19.8 ml, 113 mmol, 3 equiv.) and Propylphosphonic anhydride solution (50% in ethyl acetate) (36.1 g, 33.8 ml, 56.7 mmol, 1.5 equiv.) were added drop wise at room temperature. The mixture was stirred at room temperature for 30 minutes. The reaction mixture was extracted with saturated $NaHCO_3$-solution and two times with ethyl acetate. The organic layers were extracted with water, dried over sodium sulfate and evaporated to dryness. The desired tert-butyl N-[(1RS)-2-oxo-1-phenyl-2-(thiazol-2-ylamino)ethyl]carbamate (12 g, 95% yield) was obtained as a light yellow solid, MS: m/e=334.5 $(M+H^+)$.

Step 2: (2RS)-2-Amino-2-phenyl-N-thiazol-2-yl-acetamide hydrochloride tert-Butyl N-[(1RS)-2-oxo-1-phenyl-2-(thiazol-2-ylamino)ethyl]carbamate (Example 1, step 1) (12 g, 37 mmol) was dissolved in 100 ml of MeOH and HCl (4N in dioxane) (27.7 ml, 111 mmol, 3 equiv.) was added at room temperature. The mixture was stirred for 5 hours at room temperature. The reaction mixture was evaporated to dryness and used directly in the next step. The desired (2RS)-2-amino-2-phenyl-N-thiazol-2-yl-acetamide hydrochloride (quantitative yield) was obtained as a grey solid, MS: m/e=234.4 $(M+H^+)$.

Step 3: (2RS)-2-(6-Iodo-1-oxo-isoindolin-2-yl)-2-phenyl-N-thiazol-2-yl-acetamide (2RS)-2-Amino-2-phenyl-N-thiazol-2-yl-acetamide hydrochloride (Example 1, step 2) (1.22 g, 4.51 mmol) was dissolved in 15 ml of dioxane and 2.5 ml of DMA. Methyl 2-(bromomethyl)-5-iodobenzoate (CAS 1310377-56-0) (1.6 g, 4.51 mmol, 1 equiv.) and triethylamine (2.28 g, 3.14 ml, 22.5 mmol, 5 equiv.) were added at room temperature. The mixture was stirred at 100° C. for 2 hours. The reaction mixture was extracted with water and two times with ethyl acetate. The organic layers were extracted with brine, dried over sodium sulfate and evaporated to dryness. The crude product was purified by flash chromatography on a silica gel column eluting with an ethyl acetate:heptane 0:100 to 100:0 gradient to obtain the desired (2RS)-2-(6-iodo-1-oxo-isoindolin-2-yl)-2-phenyl-N-thiazol-2-yl-acetamide (870 mg, 41% yield) as a yellow solid, MS: m/e=475.9 (M+H$^+$).

Step 4: (2RS)-2-[1-Oxo-6-(2-phenylethynyl)isoindolin-2-yl]-2-phenyl-N-thiazol-2-yl-acetamide (2RS)-2-(6-Iodo-1-oxo-isoindolin-2-yl)-2-phenyl-N-thiazol-2-yl-acetamide (Example 1, step 3) (50 mg, 0.105 mmol) and phenylacetylene (16.1 mg, 17.3 ul, 0.158 mmol, 1.5 equiv.) were dissolved in 2 ml of THF. Triethylamine (16 mg, 22 ul, 0.158 mmol, 1.5 equiv.), bis-(triphenylphosphine)-palladium(II)dichloride (3.7 mg, 0.005 mmol, 0.05 equiv.), triphenylphosphine (2.8 mg, 0.01 mmol, 0.1 equiv.) and copper(I)iodide (0.2 mg, 0.001 mmol, 0.01 equiv.) were added and the mixture was stirred for 2 hours at 60° C. The reaction mixture was evaporated to dryness and the crude product was purified by flash chromatography on a silica gel column eluting with an ethyl acetate:heptane 0:100 to 100:0 gradient. The desired (2RS)-2[1-oxo-6-(2-phenylethynyl)isoindolin-2-yl]-2-phenyl-N-thiazol-2-yl-acetamide (30 mg, 63% yield) was obtained as a light brown solid, MS: m/e=450.0 (M+H$^+$).

Example 2

(2RS)-2-[1-oxo-6-[2-(3-pyridyl)ethynyl]isoindolin-2-yl]-2-phenyl-N-thiazol-2-yl-acetamide The title compound was obtained as a light yellow solid, MS: m/e=451.4 (M+H$^+$), using chemistry similar to that described in Example 1, step 4 starting from (2RS)-2-(6-iodo-1-oxo-isoindolin-2-yl)-2-phenyl-N-thiazol-2-yl-acetamide (Example 1, step 3) and 3-ethynylpyridine.

Example 3

(2RS)-2-[6-[2-(6-Amino-3-pyridyl)ethynyl]-1-oxo-isoindolin-2-yl]-2-phenyl-N-thiazol-2-yl-acetamide The title compound was obtained as a white foam, MS: m/e=466.6 (M+H$^+$), using chemistry similar to that described in Example 1, step 4 starting from (2RS)-2-(6-iodo-1-oxo-isoindolin-2-yl)-2-phenyl-N-thiazol-2-yl-acetamide (Example 1, step 3) and 5-ethynylpyridin-2-amine.

Example 4

(2RS)-2-[6-[2-(6-Amino-3-pyridyl)ethynyl]-1-oxo-isoindolin-2-yl]-2-(3-fluorophenyl)-N-thiazol-2-yl-acetamide Step 1: tert-Butyl N-[(1RS)-1-(3-fluorophenyl)-2-oxo-2-(thiazol-2-ylamino)ethyl]carbamate The title compound was obtained as a white solid, MS: m/e=352.4 (M+H$^+$), using chemistry similar to that described in Example 1, step 1 starting from (2RS)-2-(tert-butoxycarbonylamino)-2-(3-fluorophenyl)acetic acid and thiazol-2-amine.

Step 2: (2RS)-2-Amino-2-(3-fluorophenyl)-N-thiazol-2-yl-acetamide hydrochloride

The title compound was obtained as a white solid, MS: m/e=252.4 (M+H$^+$), using chemistry similar to that described in Example 1, step 2 starting from tert-butyl N-[(1RS)-1-(3-fluorophenyl)-2-oxo-2-(thiazol-2-ylamino)ethyl]carbamate (Example 4, step 1).

Step 3: (2RS)-2-(6-Bromo-1-oxo-isoindolin-2-yl)-2-(3-fluorophenyl)-N-thiazol-2-yl-acetamide The title compound was obtained as a light yellow foam, MS: m/e=446.4/448.4 (M+H$^+$), using chemistry similar to that described in Example 1, step 3 starting from (2RS)-2-amino-2-(3-fluorophenyl)-N-thiazol-2-yl-acetamide hydrochloride (Example 4, step 2) and methyl 5-bromo-2-(bromomethyl)benzoate Step 4: (2RS)-2-[6-[2-(6-Amino-3-pyridyl)ethynyl]-1-oxo-isoindolin-2-yl]-2-(3-fluorophenyl)-N-thiazol-2-yl-acetamide The title compound was obtained as a light yellow solid, MS: m/e=484.5 (M+H$^+$), using chemistry similar to that described in Example 1, step 4 starting from (2RS)-2-(6-bromo-1-oxo-isoindolin-2-yl)-2-(3-fluorophenyl)-N-thiazol-2-yl-acetamide (Example 4, step 3) and 5-ethynylpyridin-2-amine.

Example 5

(2RS)-2-[6-[2-(6-Amino-3-pyridyl)ethynyl]-1-oxo-isoindolin-2-yl]-2-(2,5-difluorophenyl)-N-thiazol-2-yl-acetamide Step 1: tert-Butyl N-[(1RS)-1-(2, 5 -difluorophenyl)-2-oxo-2-(thiazol-2-ylamino)ethyl]carbamate The title compound was obtained as a light yellow solid, MS: m/e=370.5 (M+H$^+$), using chemistry similar to that described in Example 1, step 1 starting from (2RS)-2-(tert-butoxycarbonylamino)-2-(2,5-difluorophenyl)acetic acid and thiazol-2-amine.

Step 2: (2RS)-2-Amino-2-(2,5-difluorophenyl)-N-thiazol-2-yl-acetamide hydrochloride The title compound was obtained as a white solid, MS: m/e=270.5 (M+H$^+$), using chemistry similar to that described in Example 1, step 2 starting from tert-butyl N-[(1RS)-1-(2,5-difluorophenyl)-2-oxo-2-(thiazol-2-ylamino)ethyl]carbamate (Example 5, step 1).

Step 3: (2RS)-2-(6-Bromo-1-oxo-isoindolin-2-yl)-2-(2,5-difluorophenyl)-N-thiazol-2-yl-acetamide The title compound was obtained as a light yellow foam, MS: m/e=464.4/466.4 (M+H$^+$), using chemistry similar to that described in Example 1, step 3 starting from (2RS)-2-amino-2-(2,5-difluorophenyl)-N-thiazol-2-yl-acetamide hydrochloride (Example 5, step 2) and methyl 5-bromo-2-(bromomethyl)benzoate Step 4: (2RS)-2-[6-[2-(6-Amino-3-pyridyl)ethynyl]-1-oxo-isoindolin-2-yl]-2-(2,5-difluorophenyl)-N-thiazol-2-yl-acetamide The title compound was obtained as a light yellow solid, MS: m/e=502.5 (M+H$^+$), using chemistry similar to that described in Example 1, step 4 starting from (2RS)-2-(6-bromo-1-oxo-isoindolin-2-yl)-2-(2,5-difluorophenyl)-N-thiazol-2-yl-acetamide (Example 5, step 3) and 5-ethynylpyridin-2-amine.

Example 6

(2RS)-2-[6-[2-[4-(Aminomethyl)phenyl]ethynyl]-1-oxo-isoindolin-2-yl]-2-phenyl-N-thiazol-2-yl-acetamide The title compound was obtained as a white solid, MS: m/e=479.6 (M+H$^+$), using chemistry similar to that described in Example 1, step 4 starting from (2RS)-2-(6-iodo-1-oxo-isoindolin-2-yl)-2-phenyl-N-thiazol-2-yl-acetamide (Example 1, step 3) and (4-ethynylphenyl)methanamine hydrochloride.

Example 7

(2RS)-2-[6-[2-(6-Acetamido-3-pyridyl)ethynyl]-1-oxo-isoindolin-2-yl]-2-phenyl-N-thiazol-2-yl-acetamide The title compound was obtained as a white semisolid, MS: m/e=508.5 (M+H$^+$), using chemistry similar to that described in Example 1, step 1 starting from (2RS)-2-[6-[2-(6-amino-3-pyridyl)ethynyl]-1-oxo-isoindolin-2-yl]-2-phenyl-N-thiazol-2-yl-acetamide (Example 3) and acetic acid.

Example 8

(2RS)-2-[6-[2-(6-Amino-3-pyridyl)ethynyl]-1-oxo-isoindolin-2-yl]-2-(1,4,5,6-tetrahydrocyclopenta[c]pyrazol-3-yl)-N-thiazol-2-yl-acetamide Step 1: 1-((2-(Trimethylsilyl)ethoxy)methyl)-1,4,5,6-tetrahydrocyclopenta[c]pyrazole-3-carbaldehyde 1,4,5,6-tetrahydrocyclopenta[c]pyrazole-3-carbaldehyde (1 g, 7.53 mmol) was dissolved in 10 ml of DCM. Hunig's Base (1.95 g, 2.63 ml, 15.1 mmol, 2 equiv.) and (2-(chloromethoxy)ethyl)trimethylsilane (1.63 g, 1.73 ml, 9.8 mmol, 1.3 equiv.) were added drop wise at room temperature. The mixture was stirred at room temperature for 70 hours. The reaction mixture was extracted with saturated NaHCO$_3$-solution and two times with DCM. The organic layers were dried over sodium sulfate and evaporated to dryness. The crude product was purified by flash chromatography on a silica gel column eluting with an ethyl acetate:heptane 0:100 to 50:50 gradient to obtain the desired 1-((2-(trimethylsilyl)ethoxy)methyl)-1,4,5,6-tetrahydrocyclopenta[c]pyrazole-3-carbaldehyde (1.6 g, 80% yield) as a colorless oil, MS: m/e=267.4 (M+H$^+$).

Step 2: (2RS)-2-(6-Bromo-1-oxo-isoindolin-2-yl)-2-[1-(2-trimethylsilylethoxymethyl)-5,6-dihydro-4H-cyclopenta[c]pyrazol-3-yl]acetonitrile 1-((2-(Trimethylsilyl)ethoxy)methyl)-1,4,5,6-tetrahydrocyclopenta[c]pyrazole-3-carbaldehyde (Example 8, step 1) (1.6 g, 6.02 mmol) was dissolved in 20 ml of acetonitrile. Methyl 2-(aminomethyl)-5-bromobenzoate hydrochloride (1.69 g, 6.02 mmol, 1 equiv.), Hunig's Base (1.95 g, 2.63 ml, 15.1 mmol, 2.5 equiv.) and trimethylsilyl cyanide (0.7 g, 0.96 ml, 7.22 mmol, 1.2 equiv.) were added at room temperature. The mixture was stirred for 17 hours at 75° C. The reaction mixture was extracted with saturated NH$_4$Cl-solution and two times with ethyl acetate. The organic layers were extracted with water and brine, dried over sodium sulfate and evaporated to dryness. The crude product was purified by flash chromatography on a silica gel column eluting with an ethyl acetate:heptane 0:100 to 50:50 gradient to obtain the desired (2RS)-2-(6-bromo-1-oxo-isoindolin-2-yl)-2-[1-(2-trimethyl silylethoxymethyl)-5,6-dihydro-4H-cyclopenta[c]pyrazol-3-yl]acetonitrile (1.66 g, 57% yield) as a yellow solid, MS: m/e=487.5/489.5 (M+H$^+$).

Step 3: (2RS)-2-(6-Bromo-1-oxo-isoindolin-2-yl)-2-[1-(2-trimethylsilylethoxymethyl)-5,6-dihydro-4H-cyclopenta[c]pyrazol-3-yl]acetic acid (2RS)-2-(6-Bromo-1-oxo-isoindolin-2-yl)-2-[1-(2-trimethylsilylethoxymethyl)-5,6-dihydro-4H-cyclopenta[c]pyrazol-3-yl]acetonitrile (Example 8, step 2) (1.66 g, 3.4 mmol) was dissolved in 12 ml of ethanol. KOH (2M in water) (8.5 ml, 17 mmol, 5 equiv.) was added at room temperature. The mixture was stirred for 4 hours at 100° C. The reaction mixture was cooled to room temperature and neutralized to pH 5 with 8 ml of acetic acid. The mixture was extracted with two times water and two times with ethyl acetate. The organic layers were dried over sodium sulfate and evaporated to dryness. The desired (2RS)-2-(6-bromo-1-oxo-isoindolin-2-yl)-2-[1-(2-trimethyl silylethoxymethyl)-5,6-dihydro-4H-cyclopenta[c]pyrazol-3-yl]acetic acid (1.7 g, 78% yield, 80% purity) was obtained as a light yellow foam, MS: m/e=506.4/508.5 (M+H$^+$).

Step 4: (2RS)-2-(6-Bromo-1-oxo-isoindolin-2-yl)-N-thiazol-2-yl-2-[1-(2-trimethylsilylethoxymethyl)-5,6-dihydro-4H-cyclop enta[c]pyrazol-3-yl]acetamide The title compound was obtained as a yellow foam, MS: m/e=588.5/590.5 (M+H$^+$), using chemistry similar to that described in Example 1, step 1 starting from (2RS)-2-(6-bromo-1-oxo-isoindolin-2-yl)-2-[1-(2-trimethyl silylethoxymethyl)-5,6-dihydro-4H-cyclopenta[c]pyrazol-3-yl] acetic acid (Example 8, step 3) and thiazol-2-amine.

Step 5: (2RS)-2-[6-[2-(6-Amino-3-pyridyl)ethynyl]-1-oxo-isoindolin-2-yl]-N-thiazol-2-yl-2-[1-(2-trimethylsilylethoxymethyl)-5,6-dihydro-4H-cyclopenta[c]pyrazol-3-yl]acetamide The title compound was obtained as a white semisolid, MS: m/e=626.7 (M+H$^+$), using chemistry similar to that described in Example 1, step 4 starting from (2RS)-2-(6-bromo-1-oxo-isoindolin-2-yl)-N-thiazol-2-yl-2-[1-(2-trimethylsilylethoxymethyl)-5,6-dihydro-4H-cyclopenta[c]pyrazol-3-yl]acetamide (Example 8, step 4) and 5-ethynylpyridin-2-amine.

Step 6: (2RS)-2-[6-[2-(6-Amino-3 -pyridyl)ethynyl]-1-oxo-isoindolin-2-yl]-2-(1,4,5,6-tetrahydrocyclopenta[c]pyrazol-3-yl)-N-thiazol-2-yl-acetamide The title compound was obtained as a white semisolid, MS: m/e=496.1 (M+H$^+$), using chemistry similar to that described in Example 1, step 2 starting from (2RS)-2-[6-[2-(6-amino-3-pyridyl)ethynyl]-1-oxo-isoindolin-2-yl]-N-thiazol-2-yl-2-[1-(2-trimethylsilylethoxymethyl)-5,6-dihydro-4H-cyclopenta[c]pyrazol-3-yl]acetamide (Example 8, step 5).

Example 9

N-Methyl-5-[2-[3-oxo-2-[(1RS)-2-oxo-1-phenyl-2-(thiazol-2-ylamino)ethyl]isoindolin-5-yl]ethynyl]pyridine-2-carboxamide Step 1: 5-[2[-3-Oxo-2-[(1RS)-2-oxo-1-phenyl-2-(thiazol-2-ylamino)ethyl]isoindolin-5-yl]ethynyl]pyridine-2-carboxylic acid The title compound was obtained as a light green solid, MS: m/e=495.5 (M+H$^+$), using chemistry similar to that described in Example 1, step 4 starting from (2RS)-2-(6-iodo-1-oxo-isoindolin-2-yl)-2-phenyl-N-thiazol-2-yl-acetamide (Example 1, step 3) and 5-ethynylpicolinic acid.

Step 2: N-Methyl-5-[2-[3-oxo-2-[(1RS)-2-oxo-1-phenyl-2-(thiazol-2-ylamino)ethyl]isoindolin-5-yl]ethynyl]pyridine-2-carboxamide The title compound was obtained as a white solid, MS: m/e=508.5 (M+H$^+$), using chemistry similar to that described in Example 1, step 1 starting from 5-[2-[3-oxo-2-[(1RS)-2-oxo-1-phenyl-2-(thiazol-2-ylamino)ethyl]isoindolin-5-yl]ethynyl]pyridine-2-carboxylic acid (Example 9, step 1) and methylamine.

Example 10

(2RS)-2-[1-Oxo-6-[2-[4-(piperazin-1-ylmethyl)phenyl]ethynyl]isoindolin-2-yl]-2-phenyl-N-thiazol-2-yl-acetamide hydrochloride Step 1: tert-Butyl 4-(4-ethynylbenzyl)piperazine-1-carboxylate 4-Ethynylbenzaldehyde (400 mg, 3.07 mmol) was dissolved in 15 ml of DCM. tert-Butyl piperazine-1-carboxylate (687 mg, 3.7 mmol, 1.2 equiv.) and sodium triacetoxyhydroborate (780 mg, 3.7 mmol, 1.2 equiv.) were added at room temperature. The mixture was stirred at room temperature for 16 hours. The reaction mixture was extracted with water and two times with DCM. The organic layers were extracted with brine, dried over sodium sulfate and evaporated to dryness. The crude product was purified by flash chromatography on a silica gel column eluting with an ethyl acetate:heptane 0:100 to 50:50 gradient to obtain the desired tert-butyl 4-(4-ethynylbenzyl)piperazine-1-carboxylate (670 mg, 73% yield) as a colorless oil, MS: m/e=301.5 (M+H$^+$).

Step 2: tert-Butyl 4-[[4-[2-[3-oxo-2-[(1RS)-2-oxo-1-phenyl-2-(thiazol-2-ylamino)ethyl]isoindolin-5-yl]ethynyl]phenyl]methyl]piperazine-1-carboxylate The title compound was obtained as an orange solid, MS: m/e=648.9 (M+H$^+$), using chemistry similar to that described in Example 1, step 4 starting from (2RS)-2-(6-iodo-1-oxo-isoindolin-2-yl)-2-phenyl-N-thiazol-2-yl-acetamide (Example 1, step 3) and tert-butyl 4-(4-ethynylbenzyl)piperazine-1-carboxylate (Example 10, step 1).

Step 3: (2RS)-2-[1-Oxo-6-[2-[4-(piperazin-1-ylmethyl)phenyl]ethynyl]isoindolin-2-yl]-2-phenyl-N-thiazol-2-yl-acetamide hydrochloride The title compound was obtained as a light brown solid, MS: m/e=546.5 (M+H$^+$), using chemistry similar to that described in Example 1, step 2 starting from tert-butyl 4-[[4-[2-[3-oxo-2-[(1RS)-2-oxo-1-phenyl-2-(thiazol-2-ylamino)ethyl]isoindolin-5-yl]ethynyl]phenyl]methyl]piperazine-1-carboxylate (Example 10, step 2).

Example 11

(2RS)-2-[6-[2-[4-(Morpholinomethyl)phenyl]ethynyl]-1-oxo-isoindolin-2-yl]-2-phenyl-N-thiazol-2-yl-acetamide Step 1: (2RS)-2-[6-[2-(4-Formylphenyl)ethynyl]-1-oxo-isoindolin-2-yl]-2-phenyl-N-thiazol-2-yl-acetamide The title compound was obtained as an orange solid, MS: m/e=478.6 (M+H$^+$), using chemistry similar to that described in Example 1, step 4 starting from (2RS)-2-(6-iodo-1-oxo-isoindolin-2-yl)-2-phenyl-N-thiazol-2-yl-acetamide (Example 1, step 3) and 4-ethynylbenzaldehyde.

Step 2: (2RS)-2-[6-[2-[4-(Morpholinomethyl)phenyl]ethynyl]-1-oxo-isoindolin-2-yl]-2-phenyl-N-thiazol-2-yl-acetamide The title compound was obtained as a white solid, MS: m/e=549.7 (M+H$^+$), using chemistry similar to that described in Example 10, step 1 starting from (2RS)-2-[6-[2-(4-formylphenyl)ethynyl]-1-oxo-isoindolin-2-yl]-2-phenyl-N-thiazol-2-yl-acetamide (Example 11, step 1) and morpholine.

Example 12

(2RS)-2-[6-[2-[4-[(4-acetylpiperazin-1-yl)methyl]phenyl]ethynyl]-1-oxo-isoindolin-2-yl]-2-phenyl-N-thiazol-2-1-acetamide The title compound was obtained as a white solid, MS: m/e=588.6 (M+H$^+$), using chemistry similar to that described in Example 1, step 1 starting from (2RS)-2-[1-oxo-6-[2-[4-(piperazin-1-ylmethyl)phenyl]ethynyl]isoindolin-2-yl]-2-phenyl-N-thiazol-2-yl-acetamide hydrochloride (Example 10) and acetic acid.

Example 13

(2RS)-2-[6-[2-[4-[(4-Ethylpiperazin-1-yl)methyl]phenyl]ethynyl]-1-oxo-isoindolin-2-yl]-2-phenyl-N-thiazol-2-yl-acetamide (2RS)-2-[1-Oxo-6-[2-[4-(piperazin-1-ylmethyl)phenyl]ethynyl]isoindolin-2-yl]-2-phenyl-N-thiazol-2-yl-acetamide hydrochloride (Example 10) (30 mg, 0.05 mmol) was dissolved in 1 ml of acetonitrile. Potassium carbonate (57 mg, 0.41 mmol, 8 equiv.) and iodoethane (9.6 mg, 0.06 mmol, 1.2 equiv.) were added at room temperature. The mixture was stirred at 65° C. for 4 hours. The reaction mixture was extracted with water and two times with DCM. The organic layers were extracted with brine, dried over sodium sulfate and evaporated to dryness. The crude product was purified by flash chromatography on a silica gel column eluting with a dichloromethane:methanol 100:0 to 85:15 gradient to obtain the desired (2RS)-2-[6-[2-[4-[(4-ethylpiperazin-1-yl)methyl]phenyl]ethynyl]-1-oxo-isoindolin-2-yl]-2-phenyl-N-thiazol-2-yl-acetamide (13 mg, 44% yield) as a colorless solid, MS: m/e=576.8 (M+H$^+$).

Example 14

(2RS)-2-[6-[2-[6-(Morpholine-4-carbonyl)-3-pyridyl]ethynyl]-1-oxo-isoindolin-2-yl]-2-phenyl-N-thiazol-2-yl-acetamide The title compound was obtained as a light yellow solid, MS: m/e=564.6 (M+H$^+$), using chemistry similar to that described in Example 1, step 1 starting from 5-[2-[3-oxo-2-[(1RS)-2-oxo-1-phenyl-2-(thiazol-2-ylamino)ethyl]isoindolin-5-yl]ethynyl]pyridine-2-carboxylic acid (Example 9, step 1) and morpholine.

Example 15

(2RS)-2-[6-[2-(6-Amino-3-pyridyl)ethynyl]-1-oxo-isoindolin-2-yl]-2-(5-fluoro-2-hydroxy-phenyl)-N-thiazol-2-yl-acetamide Step 1: tert-Butyl [(1RS)-1-(5-fluoro-2-methoxyphenyl)-2-oxo-2-(thiazol-2-ylamino)ethyl]carbamate The title compound was obtained as a white solid, MS: m/e=382.5 (M+H$^+$), using chemistry similar to that described in Example 1, step 1 starting from (2RS)-2-((tert-butoxycarbonyl)amino)-2-(5-fluoro-2-methoxyphenyl)acetic acid.

Step 2: (2RS)-2-Amino-2-(5-fluoro-2-methoxyphenyl)-N-(thiazol-2-yl)acetamide hydrochloride The title compound was obtained as a light green solid, MS: m/e=282.4 (M+H$^+$), using chemistry similar to that described in Example 1, step 2 starting from tert-butyl

[(1RS)-1-(5-fluoro-2-methoxyphenyl)-2-oxo-2-(thiazol-2-ylamino)ethyl]carbamate (Example 15, step 1).

Step 3: (2RS)-2-(5-Fluoro-2-methoxyphenyl)-2-(6-iodo-1-oxoi soindolin-2-yl)-N-(thiazol-2-yl)acetamide The title compound was obtained as a white solid, MS: m/e=524.4 (M+H⁺), using chemistry similar to that described in Example 1, step 3 starting from (2RS)-2-amino-2-(5-fluoro-2-methoxyphenyl)-N-(thiazol-2-yl)acetamide hydrochloride (Example 15, step 2) and methyl 2-(bromomethyl)-5-iodobenzoate.

Step 4: (2RS)-2-(6-((6-Aminopyridin-3-yl)ethynyl)-1-oxoisoindolin-2-yl)-2-(5-fluoro-2-methoxyphenyl)-N-(thiazol-2-yl)acetamide The title compound was obtained as a light yellow oil, MS: m/e=514.6 (M+H⁺), using chemistry similar to that described in Example 1, step 4 starting from (2RS)-2-(5-fluoro-2-methoxyphenyl)-2-(6-iodo-1-oxoisoindolin-2-yl)-N-(thiazol-2-yl)acetamide (Example 15, step 3) and 5-ethynylpyridin-2-amine.

Step 5: (2RS)-2-[6[2-(6-Amino-3-pyridyl)ethynyl]-1-oxo-isoindolin-2-yl]-2-(5-fluoro-2-hydroxy-phenyl)-N-thiazol-2-yl-acetamide (2RS)-2-(6-((6-Aminopyridin-3-yl)ethynyl)-1-oxoisoindolin-2-yl)-2-(5-fluoro-2-methoxyphenyl)-N-(thiazol-2-yl)acetamide (Example 15, step 4) (80 mg, 0.16 mmol) was dissolved in 2.5 ml of dichloromethane. BBr3 (1M in dichloromethane) (0.62 ml, 0.62 mmol, 4 equiv.) was added at room temperature. The mixture was stirred at 25° C. for 1 hour. The reaction mixture was quenched with water (56 mg, 3.1 mmol, 20 equiv.) and the crude product solution was purified directly by flash chromatography on a silica gel column eluting with a dichloromethane:methanol 100:0 to 80:20 gradient to obtain the desired (2RS)-2-[6-[2-(6-amino-3-pyridyl)ethynyl]-1-oxo-isoindolin-2-yl]-2-(5-fluoro-2-hydroxy-phenyl)-N-thiazol-2-yl-acetamide (56 mg, 72% yield) as a light yellow solid, MS: m/e=500.0 (M+H⁺).

Example 16

(2RS)-2-(5-Fluoro-2-hydroxy-phenyl)-2-[1-oxo-6-[2-(3-pyridyl)ethynyl]isoindolin-2-yl]-N-thiazol-2-yl-acetamide Step 1: Methyl (2RS)-2-(6-bromo-1-oxo-isoindolin-2-yl)-2-(5-fluoro-2-methoxy-phenyl)acetate 6-Bromoisoindolin-1-one (CAS 675109-26-9) (1.61 g, 7.58 mmol, 1.05 equiv.) was suspended in 32 ml of THF and cooled to 0-5° C. Sodium hydride (60% dispersion in mineral oil) (318 mg, 7.94 mmol, 1.1 equiv.) was added at 0-5° C. The reaction mixture was stirred at room temperature for 15 minutes and then cooled to 0-5° C. Methyl (2RS)-2-bromo-2-(5-fluoro-2-methoxyphenyl)acetate (CAS 1368458-30-3) (2.00 g, 7.22 mmol) dissolved in 8.0 ml of THF was added dropwise at 0-5° C. After the addition was complete, the ice bath was removed and the reaction mixture was stirred at room temperature for 2 hours. The reaction mixture was quenched with saturated NH₄Cl-solution and extracted with ethyl acetate. The aqueous layer was backextracted with ethyl acetate. The organic layers were washed with water and brine. The organic layers were combined, dried over sodium sulfate, filtered and evaporated to dryness. The crude product was purified by flash chromatography on a silica gel column eluting with an ethyl acetate:heptane 0:100 to 50:50 gradient to obtain the desired methyl (2RS)-2-(6-bromo-1-oxo-isoindolin-2-yl)-2-(5-fluoro-2-methoxy-phenyl)acetate (2.202 g, 75% yield) as a yellow foam, MS: m/e=408.0/410.0 (M+H⁺).

Step 2: (2RS)-2-(6-Bromo-1-oxo-isoindolin-2-yl)-2-(5-fluoro-2-methoxy-phenyl)acetic acid Methyl (2RS)-2-(6-bromo-1-oxo-isoindolin-2-yl)-2-(5-fluoro-2-methoxy-phenyl)acetate (Example 16, step 1) (2.200 g, 5.39 mmol) was dissolved in 10 ml of THF and 10 ml of methanol. Lithium hydroxide monohydrate (678 mg, 16.2 mmol, 3 equiv.) was added followed by 10 ml of water and the reaction mixture was stirred at room temperature for 2 hours. The organic solvents were removed under reduced pressure. The aqueous residue was acidified with 5% Citric acid-solution and then extracted with ethyl acetate. The aqueous layer was backextracted with ethyl acetate. The organic layers were washed with water and brine. The organic layers were combined, dried over sodium sulfate, filtered and evaporated to dryness. The desired (2RS)-2-(6-bromo-1-oxo-isoindolin-2-yl)-2-(5-fluoro-2-methoxy-phenyl)acetic acid (2.056 g, 97% yield) was obtained as a yellow solid, MS: m/e=394.1/396.1 (M+H⁺).

Step 3: (2RS)-2-(6-Bromo-1-oxo-isoindolin-2-yl)-2-(5-fluoro-2-methoxy-phenyl)-N-thiazol-2-yl-acetamide (2RS)-2-(6-Bromo-1-oxo-isoindolin-2-yl)-2-(5-fluoro-2-methoxy-phenyl)acetic acid (Example 16, step 2) (2.050 g, 5.2 mmol) and thiazol-2-amine (651 mg, 6.5 mmol, 1.3 equiv.) were dissolved in 13 ml of DMF. Hunig's base (2.81 g, 3.8 ml, 21.8 mmol, 4.2 equiv.) was added followed by TBTU (2 g, 6.24 mmol, 1.2 equiv.). The reaction mixture was stirred at room temperature for 4 days. The reaction mixture was diluted with water (a precipitate was formed). The suspension was cooled to 0-5° C. and stirred for 30 minutes. The cold suspension was filtered and rinsed with water and a minimal amount of ethyl acetate. The resulting off-white solid was dried using the rotavap and then put under high vacuum to afford (2RS)-2-(6-bromo-1-oxo-isoindolin-2-yl)-2-(5-fluoro-2-methoxy-phenyl)-N-thiazol-2-yl-acetamide (2.210 g, 89% yield), MS: m/e=476.0/478.0 (M+H⁺).

Step 4: (2RS)-2-(5-Fluoro-2-methoxy-phenyl)-2-[1-oxo-6-[2-(3-pyridyl)ethynyl]isoindolin-2-yl]-N-thiazol-2-yl-acetami de (2RS)-2-(6-Bromo-1-oxo-i soindolin-2-yl)-2-(5-fluoro-2-methoxy-phenyl)-N-thiazol-2-yl-acetamide (Example 16, step 3) (110 mg, 0.231 mmol) was dissolved in 2.3 ml of DMF and 3-ethynylpyridine (35 mg, 0.339 mmol, 1.5 equiv.), triethylamine (72.6 mg, 0.10 ml, 0.717 mmol, 3.1 equiv.), triphenylphosphine (6 mg, 0.023 mmol, 0.10 equiv.), bis(triphenylphosphine)-palladium (II) dichloride (8 mg, 0.0114 mmol, 0.05 equiv.) and copper (I) iodide (2 mg, 0.0105 mmol, 0.05 equiv.) were added and the reaction mixture was stirred at 90° C. for 6 hours. The reaction mixture was cooled to room temperature and extracted with ethyl acetate and water. The aqueous layer was backextracted twice with ethyl acetate. The organic layers were washed four times with water and once with brine. The organic layers were combined, dried over sodium sulfate, filtered and evaporated to dryness. The crude product was adsorbed on isolute® and purified by flash chromatography on a silica gel column eluting with a dichloromethane:methanol 100:0 to 95:5 gradient to obtain the desired (2RS)-2-(5-fluoro-2-methoxy-phenyl)-2-[1-oxo-6-[2-(3-pyridyl)ethynyl]isoindolin-2-yl]-N-thiazol-2-yl-acetamide (61 mg, 53% yield) as a light yellow solid, MS: m/e=499.2 (M+H⁺).

Step 5: (2RS)-2-(5-Fluoro-2-hydroxy-phenyl)-2-[41-oxo-6-[2-(3-pyridypethynyl]isoindolin-2-yl]-N-thiazol-2-yl-acetamide The title compound was obtained as an off-white solid, MS: m/e=485.1 (M+H⁺), using chemistry similar to that described in Example 15, step 5 starting from (2RS)-2-(5-fluoro-2-methoxy-phenyl)-2-[1-oxo-6-[2-(3-pyridyl)ethynyl]isoindolin-2-yl]-N-thiazol-2-yl-acetamide (Example 16, step 4).

Example 17

(2RS)-2-(5-Fluoro-2-hydroxy-phenyl)-2-[1-oxo-6-(2-phenylethynyl)isoindolin-2-yl]-N-thiazol-2-yl-acetamide Step 1: (2RS)-2-(5-Fluoro-2-hydroxy-phenyl)-2-(6-iodo-1-oxo-isoindolin-2-yl)-N-thiazol-2-yl-acetamide The title compound was obtained as an off-white solid, MS: m/e=510.0 (M+H$^+$), using chemistry similar to that described in Example 15, step 5 starting from (2RS)-2-(5-fluoro-2-methoxy-phenyl)-2-(6-iodo-1-oxo-isoindolin-2-yl)-N-thiazol-2-yl-acetamide (Example 15, step 3).

Step 2: (2RS)-2-[2-[tert-Butyl(dimethyl)silyl]oxy-5-fluoro-phenyl]-2-(6-iodo-1-oxo-isoindolin-2-yl)-N-thiazol-2-yl-acetamide (2RS)-2-(5-Fluoro-2-hydroxy-phenyl)-2-(6-iodo-1-oxo-isoindolin-2-yl)-N-thiazol-2-yl-acetamide (Example 17, step 1) (315 mg, 0.619 mmol) was dissolved in 2.0 ml of DMF. tert-Butyldimethylchlorosilane (103 mg, 0.680 mmol, 1.1 equiv.) was added followed by imidazole (50 mg, 0.734 mmol, 1.2 equiv.). The reaction mixture was stirred at room temperature for 16 hours. Additional tert-butyldimethylchlorosilane (34 mg, 0.226 mmol, 0.365 equiv.) was added followed by imidazole (17 mg, 0.250 mmol, 0.404 equiv.). The reaction mixture was stirred at room temperature for 5 hours. The reaction mixture was extracted with MTBE and water. The aqueous layer was backextracted with MTBE. The organic layers were washed three times with water and once with brine. The organic layers were combined, dried over sodium sulfate, filtered and evaporated to dryness. The crude product was adsorbed on isolute® and purified by flash chromatography on a silica gel column eluting with an ethyl acetate:heptane 0:100 to 50:50 gradient to obtain the desired (2RS)-2-[2-[tert-butyl(dimethyl)silyl]oxy-5-fluoro-phenyl]-2-(6-iodo-1-oxo-isoindolin-2-yl)-N-thiazol-2-yl-acetamide (282 mg, 73% yield) as an off-white solid, MS: m/e=624.3 (M+H$^+$).

Step 3: (2RS)-2-[2-[tert-Butyl(dimethypsilyl]oxy-5-fluoro-phenyl]-2-[1-oxo-6-(2-phenylethynyl)isoindolin-2-yl]-N-thiazol-2-yl-acetamide The title compound was obtained as a yellow solid, MS: m/e=598.3 (M+H$^+$), using chemistry similar to that described in Example 1, step 4 starting from (2RS)-2-[2-[tert-butyl(dimethyl)silyl]oxy-5-fluoro-phenyl]-2-(6-iodo-1-oxo-isoindolin-2-yl)-N-thiazol-2-yl-acetamide (Example 17, step 2) and phenylacetylene.

Step 4: (2RS)-2-(5-Fluoro-2-hydroxy-phenyl)-2-[1-oxo-6-(2-phenylethynyl)isoindolin-2-yl]-N-thiazol-2-yl-acetamide (2RS)-2-[2-[tert-Butyl(dimethyl)silyl]oxy-5-fluoro-phenyl]-2-[1-oxo-6-(2-phenylethynyl)isoindolin-2-yl]-N-thiazol-2-yl-acetamide (Example 17, step 3) (45 mg, 0.075 mmol) was dissolved in 1.2 ml of THF. Tetrabutylammonium fluoride (1.0M solution in THF) (79 µl, 0.079 mmol, 1.05 equiv.) was added at room temperature and the reaction mixture was stirred at room temperature for 60 minutes. The reaction mixture was extracted with ethyl acetate and water. The aqueous layer was backextracted with ethyl acetate. The organic layers were washed three times with water and once with brine. The organic layers were combined, dried over sodium sulfate, filtered and evaporated to dryness. The crude product was adsorbed on isolute® and purified by flash chromatography on a silica gel column eluting with a dichloromethane:methanol 100:0 to 95:5 gradient to obtain the desired (2RS)-2-(5-fluoro-2-hydroxy-phenyl)-2-[1-oxo-6-(2-phenylethynyl)isoindolin-2-yl]-N-thiazol-2-yl-acetamide (27 mg, 74% yield) as a light yellow solid, MS: m/e=484.2 (M+H$^+$).

Example 18

(2RS)-2-[6-[2-(2-Aminopyrimidin-5-yl)ethynyl]-1-oxo-isoindolin-2-yl]-2-(5-fluoro-2-hydroxy-phenyl)-N-thiazol-2-yl-acetamide Step 1: (2RS)-2-[6-[2-(2-Aminopyrimidin-5-yl)ethynyl]-1-oxo-isoindolin-2-yl]-2-[2-[tert-butyl(dimethyl)silyl]oxy-5-fluoro-phenyl]-N-thiazol-2-yl-acetamide The title compound was obtained as a light yellow solid, MS: m/e=615.5 (M+H$^+$), using chemistry similar to that described in Example 1, step 4 starting from (2RS)-2-[2-[tert-butyl(dimethyl)silyl]oxy-5-fluoro-phenyl]-2-(6-iodo-1-oxo-isoindolin-2-yl)-N-thiazol-2-yl-acetamide (Example 17, step 2) and 5-ethynylpyrimidin-2-amine (CAS 857265-74-8).

Step 2: (R2S)-2-[6-[2-(2-Aminopyrimidin-5-yl)ethynyl]-1-oxo-isoindolin-2-yl]-2-(5-fluoro-2-hydroxy-phenyl)-N-thiazol-2-yl-acetamide The title compound was obtained as an off-white powder, MS: m/e=501.3 (M+H$^+$), using chemistry similar to that described in Example 17, step 4 starting from (2RS)-2-[6-[2-(2-aminopyrimidin-5-yl)ethynyl]-1-oxo-isoindolin-2-yl]-2-[2-[tert-butyl(dimethyl)silyl]oxy-5-fluoro-phenyl]-N-thiazol-2-yl-acetamide (Example 18, step 1).

Example 19

(2RS)-2-[6-[2-(2-Chloro-4-pyridyl)ethynyl]-1-oxo-isoindolin-2-yl]-2-(5-fluoro-2-hydroxy-phenyl)-N-thiazol-2-yl-acetamide Step 1: (2RS)-2-[2-[tert-Butyl(dimethyl)silyl]oxy-5-fluoro-phenyl]-2-[6-[2-(2-chloro-4-pyridyl)ethynyl]-1-oxo-isoindolin-2-yl]-N-thiazol-2-yl-acetamide The title compound was obtained as a yellow solid, MS: m/e=633.2 (M+H$^+$), using chemistry similar to that described in Example 1, step 4 starting from (2RS)-2-[2-[tert-butyl(dimethyl)silyl]oxy-5-fluoro-phenyl]-2-(6-iodo-1-oxo-i soindolin-2-yl)-N-thiazol-2-yl-acetamide (Example 17, step 2) and 2-chloro-4-ethynylpyridine (CAS 945717-09-9).

Step 2: (2RS)-2-[6-[2-(2-Chloro-4-pyridyl)ethynyl]-1-oxo-isoindolin-2-yl]-2-(5-fluoro-2-hydroxy-phenyl)-N-thiazol-2-yl-acetamide The title compound was obtained as an off-white solid, MS: m/e=519.1 (M+H$^+$), using chemistry similar to that described in Example 17, step 4 starting from ((2RS)-2-[2-[tert-butyl(dimethyl)silyl]oxy-5-fluoro-phenyl]-2-[6-[2-(2-chloro-4-pyridyl)ethynyl]-1-oxo-isoindolin-2-yl]-N-thiazol-2-yl-acetamide (Example 19, step 1).

Example 20

(2RS)-2-[6-[2-(6-Amino-3-pyridyl)ethynyl]-1-oxo-isoindolin-2-yl]-2-(5-fluoro-2-hydroxy-phenyl)-N-(2-pyridyl)acetamide Step 1: (2RS)-2-(6-Bromo-1-oxo-isoindolin-2-yl)-2-(5-fluoro-2-methoxy-phenyl)-N-(2-pyridyl)acetamide The title compound was obtained as a light yellow solid, MS: m/e=470.2/472.2 (M+H$^+$), using chemistry similar to that described in Example 16, step 3 starting from (2RS)-

2-(6-bromo-1-oxo-isoindolin-2-yl)-2-(5-fluoro-2-methoxy-phenyl)acetic acid (Example 16, step 2) and pyridin-2-amine (CAS 504-29-0).

Step 2: (2RS)-2-[6-[2-(6-Amino-3-pyridyl)ethynyl]-1-oxo-isoindolin-2-yl]-2-(5-fluoro-2-methoxy-phenyl)-N-(2-pyridyl)acetamide The title compound was obtained as an off-white solid, MS: m/e=508.4 (M+H$^+$), using chemistry similar to that described in Example 16, step 4 starting from (2RS)-2-(6-bromo-1-oxo-isoindolin-2-yl)-2-(5-fluoro-2-methoxy-phenyl)-N-(2-pyridyl)acetamide (Example 20, step 1) and 5-ethynylpyridin-2-amine (CAS 82454-61-3).

Step 3: (2RS)-2-[6-[2-(6-Amino-3-pyridyl)ethynyl]-1-oxo-isoindolin-2-yl]-2-(5-fluoro-2-hydroxy-phenyl)-N-(2-pyridyl)acetamide The title compound was obtained as a white solid, MS: m/e=494.4 (M+H$^+$), using chemistry similar to that described in Example 15, step 5 starting from (2RS)-2-[6-[2-(6-amino-3-pyridyl)ethynyl]-1-oxo-isoindolin-2-yl]-2-(5-fluoro-2-methoxy-phenyl)-N-(2-pyridyl)acetamide (Example 20, step 2).

Example 21

(2RS)-2-[6-[2-(6-Amino-3-pyridyl)ethynyl]-7-methyl-1-oxo-isoindolin-2-yl]-2-(5-fluoro-2-hydroxy-phenyl)-N-thiazol-2-yl-acetamide Step 1: Methyl (2RS)-2-(6-bromo-7-methyl-1-oxo-isoindolin-2-yl)-2-(5-fluoro-2-methoxy-phenyl)acetate The title compound was obtained as a yellow foam, MS: m/e=422.0/424.0 (M+H$^+$), using chemistry similar to that described in Example 16, step 1 starting from methyl (2RS)-2-bromo-2-(5-fluoro-2-methoxyphenyl)acetate (CAS 1368458-30-3) and 6-bromo-7-methyl-isoindolin-1-one (CAS 1427394-72-6).

Step 2: (2RS)-2-(6-Bromo-7-methyl-1-oxo-isoindolin-2-yl)-2-(5-fluoro-2-methoxy-phenyl)acetic acid The title compound was obtained as a light yellow solid, MS: m/e=408.0/410.0 (M+H$^+$), using chemistry similar to that described in Example 16, step 2 starting from methyl (2RS)-2-(6-bromo-7-methyl-1-oxo-isoindolin-2-yl)-2-(5-fluoro-2-methoxy-phenyl)acetate (Example 21, step 1).

Step 3: (2RS)-2-(6-Bromo-7-methyl-1-oxo-isoindolin-2-yl)-2-(5-fluoro-2-methoxy-phenyl)-N-thiazol-2-yl-acetamide The title compound was obtained as an off-white solid, MS: m/e=490.0/492.0 (M+H$^+$), using chemistry similar to that described in Example 16, step 3 starting from (2RS)-2-(6-bromo-7-methyl-1-oxo-isoindolin-2-yl)-2-(5-fluoro-2-methoxy-phenyl)acetic acid (Example 21, step 2) and thiazol-2-amine.

Step 4: (2RS)-2-[6-[2-(6-Amino-3-pyridyl)ethynyl]-7-methyl-1-oxo-isoindolin-2-yl]-2-(5-fluoro-2-methoxy-phenyl)-N-thiazol-2-yl-acetamide The title compound was obtained as a light brown solid, MS: m/e=528.3 (M+H$^+$), using chemistry similar to that described in Example 16, step 4 starting from (2RS)-2-(6-bromo-7-methyl-1-oxo-isoindolin-2-yl)-2-(5-fluoro-2-methoxy-phenyl)-N-thiazol-2-yl-acetamide (Example 21, step 3) and 5-ethynylpyridin-2-amine (CAS 82454-61-3).

Step 5: (2RS)-2-[6-[2-(6-Amino-3-pyridyl)ethynyl]-7-methyl-1-oxo-isoindolin-2-yl]-2-(5-fluoro-2-hydroxy-phenyl)-N-thiazol-2-yl-ac etami de The title compound was obtained as a light yellow solid, MS: m/e=514.2 (M+H$^+$), using chemistry similar to that described in Example 15, step 5 starting from (2RS)-2-[6-[2-(6-amino-3-pyridyl)ethynyl]-7-methyl-1-oxo-isoindolin-2-yl]-2-(5-fluoro-2-methoxy-phenyl)-N-thiazol-2-yl-acetamide (Example 21, step 4).

Example 22

(2RS)-2-[6-[2-(6-Amino-3-pyridyl)ethynyl]-7-methyl1-oxo-isoindolin-2-yl]-2-(5-fluoro-2-hydroxy-phenyl)-N-(2-pyridyl)acetamide Step 1: (2RS)-2-(6-Bromo-7-methyl-1-oxo-isoindolin-2-yl)-2-(5-fluoro-2-methoxy-phenyl)-N-(2-pyridyl)acetamide The title compound was obtained as a light yellow solid, MS: m/e=484.2/486.2 (M+H$^+$), using chemistry similar to that described in Example 16, step 3 starting from (2RS)-2-(6-bromo-7-methyl-1-oxo-isoindolin-2-yl)-2-(5-fluoro-2-methoxy-phenyl)acetic acid (Example 21, step 2) and pyridin-2-amine (CAS 504-29-0).

Step 2: (2RS)-2-[6[2-(6-Amino-3-pyridyl)ethynyl]-7-methyl-1-oxo-isoindolin-2-yl]-2-(5-fluoro-2-methoxy-phenyl)-N-(2-pyridyl)acetamide The title compound was obtained as a light yellow solid, MS: m/e=522.2 (M+H$^+$), using chemistry similar to that described in Example 16, step 4 starting from (2RS)-2-(6-bromo-7-methyl-1-oxo-isoindolin-2-yl)-2-(5-fluoro-2-methoxy-phenyl)-N-(2-pyridyl)acetamide (Example 22, step 1) and 5-ethynylpyridin-2-amine (CAS 82454-61-3).

Step 3: (2RS)-2-[6-[2-(6-Amino-3-pyridyl)ethynyl]-7-methyl-1-oxo-isoindolin-2-yl]-2-(5-fluoro-2-hydroxy-phenyl)-N-(2-pyridyl)acetamide The title compound was obtained as an off-white solid, MS: m/e=508.2 (M+H$^+$), using chemistry similar to that described in Example 15, step 5 starting from (2RS)-2-[6-[2-(6-amino-3-pyridyl)ethynyl]-7-methyl-1-oxo-isoindolin-2-yl]-2-(5-fluoro-2-methoxy-phenyl)-N-(2-pyridyl)acetamide (Example 22, step 2).

Example 23

(2RS)-2-[6-[2-(6-Amino-3-pyridyl)ethynyl]-1-oxo-isoindolin-2-yl]-2-(5-chloro-2-hydroxy-phenyl)-N-thiazol-2-yl-acetamide Step 1: Methyl (2RS)-2-bromo-2-(5-chloro-2-methoxy-phenyl)acetate Methyl 2-(5-chloro-2-methoxyphenyl)acetate (CAS 26939-01-5) (1.14 g, 5.31 mmol) was dissolved in 20 ml of α,α,α-trifluorotoluene (CAS 98-08-08). N-Bromosuccinimide (1.13 g, 6.37 mmol, 1.2 equiv.) was added followed by 2,2'-azobis(2-methylpropionitrile) (AIBN) (88 mg, 0.536 mmol, 0.10 equiv.). The reaction mixture was stirred at 110° C. for 90 minutes. The reaction mixture was cooled to room temperature, adsorbed on isolute® and purified by flash chromatography on a silica gel column eluting with an ethyl acetate:heptane 0:100 to 20:80 gradient to obtain the desired methyl (2RS)-2-bromo-2-(5-chloro-2-methoxy-phenyl)acetate (1.367 g, 88% yield) as a light yellow oil, MS: m/e=293.1/295.1 (M+H$^+$).

Step 2: Methyl (2RS)-2-(6-bromo-1-oxo-isoindolin-2-yl)-2-(5-chloro-2-methoxy-phenyl)acetate The title compound was obtained as a yellow foam, MS: m/e=424.0/425.9 (M+H$^+$), using chemistry similar to that described in Example 16, step 1 starting from methyl (2RS)-2-bromo-2 -(5-chloro-2-methoxy-phenyl)acetate (Example 23, step 1) and 6-bromoisoindolin-1-one (CAS 675109-26-9).

Step 3: (2RS)-2-(6-Bromo-1-oxo-isoindolin-2-yl)-2-(5-chloro-2-methoxy-phenyl)acetic acid The title compound was obtained as a light yellow solid, MS: m/e=409.9/411.9 (M+H$^+$), using chemistry similar to that described in Example 16, step 2 starting from methyl (2RS)-2-(6-bromo-1-oxo-isoindolin-2-yl)-2-(5-chloro-2-methoxy-phenyl)acetate (Example 23, step 2).

Step 4: (2RS)-2-(6-Bromo-1-oxo-isoindolin-2-yl)-2-(5-chloro-2-methoxy-phenyl)-N-thiazol-2-yl-acetamide The title compound was obtained as an off-white solid, MS: m/e=492.0/494.0 (M+H$^+$), using chemistry similar to that described in Example 16, step 3 starting from (2RS)-2-(6-bromo-1-oxo-isoindolin-2-yl)-2-(5-chloro-2-methoxy-phenyl)acetic acid (Example 23, step 3) and thiazol-2-amine.

Step 5: (2RS)-2-[6-[2-(6-Amino-3-pyridyl)ethynyl]-1-oxo-isoindolin-2-yl]-2-(5-chloro-2-methoxy-phenyl)-N-thiazol-2-yl-acetamide The title compound was obtained as a yellow solid, MS: m/e=530.2/532.2 (M+H$^+$), using chemistry similar to that described in Example 16, step 4 starting from (2RS)-2-(6-bromo-1-oxo-isoindolin-2-yl)-2-(5-chloro-2-methoxy-phenyl)-N-thiazol-2-yl-acetamide (Example 23, step 4) and 5-ethynylpyridin-2-amine (CAS 82454-61-3).

Step 6: (2RS)-2-[6-[2-(6-Amino-3-pyridyl)ethynyl]-1-oxo-isoindolin-2-yl]-2-(5-chloro-2-hydroxy-phenyl)-N-thiazol-2-yl-acetamide The title compound was obtained as a light yellow solid, MS: m/e=516.2/518.2 (M+H$^+$), using chemistry similar to that described in Example 15, step 5 starting from (2RS)-2-[6-[2-(6-Amino-3-pyridyl)ethynyl]-1-oxo-isoindolin-2-yl]-2-(5-chloro-2-methoxy-phenyl)-N-thiazol-2-yl-acetamide (Example 23, step 5).

Example 24

(2RS)-2-[6-[2-(6-Amino-3-pyridyl)ethynyl]-1-oxo-isoindolin-2-yl]-2-(2-hydroxyphenyl)-N-thiazol-2-yl-acetamide Step 1: tert-Butyl N-[(1RS)-1-(2-methoxyphenyl)-2-oxo-2-(thiazol-2-ylamino)ethyl]carbamate The title compound was obtained as a white solid, MS: m/e=364.3 (M+H$^+$), using chemistry similar to that described in Example 16, step 3 starting from (2RS)-2-(tert-butoxycarbonylamino)-2-(2-methoxyphenyl)acetic acid (CAS 179417-69-7) and thiazol-2-amine.

Step 2: (2RS)-2-Amino-2-(2-methoxyphenyl)-N-thiazol-2-yl-acetamide hydrochloride tert-Butyl N-[(1RS)-1-(2-methoxyphenyl)-2-oxo-2-(thiazol-2-ylamino)ethyl]carbamate (Example 24, step 1) (190 mg, 0.523 mmol) was dissolved in 2 ml of dichloromethane and HCl (4N in dioxane) (1.31 ml, 5.23 mmol, 10 equiv.) was added at room temperature. The reaction mixture was stirred at room temperature for 2 hours. The reaction mixture was evaporated to dryness and used directly in the next step. The desired (2RS)-2-amino-2-(2-methoxyphenyl)-N-thiazol-2-yl-acetamide hydrochloride (quantitative yield) was obtained as a white solid, MS: m/e=264.3 (M+H$^+$).

Step 3: (2RS)-2-(6-Bromo-1-oxo-isoindolin-2-yl)-2-(2-methoxyphenyl)-N-thiazol-2-yl-acetamide (2RS)-2-Amino-2-(2-methoxyphenyl)-N-thiazol-2-yl-acetamide hydrochloride (Example 24, step 2) (160 mg, 0.534 mmol) was dissolved in 3 ml of DMF. Methyl 5-bromo-2-(bromomethyl)benzoate (CAS 79670-17-0) (197 mg, 0.640 mmol, Eq: 1.2) and triethylamine (270 mg, 0.37 ml, 2.67 mmol, 5 equiv.) were added at room temperature. The reaction mixture was stirred at 80° C. for 16 hours. The reaction mixture was extracted with water and two times with ethyl acetate. The organic layers were washed with water and brine, dried over sodium sulfate and evaporated to dryness. The crude product was purified by flash chromatography on a silica gel column eluting with a dichloromethane:methanol 100:0 to 90:10 gradient to obtain the desired (2RS)-2-(6-bromo-1-oxo-isoindolin-2-yl)-2-(2-methoxyphenyl)-N-thiazol-2-yl-acetamide (140 mg, 57% yield) as a light yellow solid, MS: m/e=458.3/460.3 (M+H$^+$).

Step 4: (2RS)-2-[6-[2-(6-Amino-3-pyridyl)ethynyl]-1-oxo-isoindolin-2-yl]-2-(2-methoxyphenyl)-N-thiazol-2-yl-acetamide The title compound was obtained as a light yellow solid, MS: m/e=496.5 (M+H$^+$), using chemistry similar to that described in Example 16, step 4 starting from (2RS)-2-(6-bromo-1-oxo-isoindolin-2-yl)-2-(2-methoxyphenyl)-N-thiazol-2-yl-acetamide (Example 24, step 3) and 5-ethynylpyridin-2-amine (CAS 82454-61-3).

Step 5: (2RS)-2-[6-[2-(6-Amino-3-pyridyl)ethynyl]-1-oxo-isoindolin-2-yl]-2-(2-hydroxyphenyl)-N-thiazol-2-yl-acetamide The title compound was obtained as a light yellow solid, MS: m/e=482.4 (M+H$^+$), using chemistry similar to that described in Example 15, step 5 starting from (2RS)-2-[6-[2-(6-amino-3-pyridyl)ethynyl]-1-oxo-isoindolin-2-yl]-2-(2-methoxyphenyl)-N-thiazol-2-yl-acetamide (Example 24, step 4).

Example 25

(2RS)-2-[6-[2-(6-Amino-3-pyridyl)ethynyl]-1-oxo-isoindolin-2-yl]-2-(3-hydroxy-2-pyridyl)-N-thiazol-2-yl-acetamide trifluoroacetate Step 1: (2RS)-2-(6-Bromo-1-oxo-isoindolin-2-yl)-2-(3-methoxy-2-pyridyl)acetonitrile The title compound was obtained as a light red solid, MS: m/e=357.9/359.9 (M+H$^+$), using chemistry similar to that described in Example 8, step 2 starting from 3-methoxypicolinaldehyde and methyl 2-(aminomethyl)-5-bromobenzoate hydrochloride.

Step 2: Sodium (2RS)-2-(6-bromo-1-oxo-isoindolin-2-yl)-2-(3-methoxy-2-pyridyl)acetate The title compound was obtained as a yellow solid, MS: m/e=376.9/378.9 (M+H$^+$), using chemistry similar to that described in Example 8, step 3 starting from (2RS )-2-(6-bromo-1-oxo-isoindolin-2-yl)-2-(3-methoxy-2-pyridyl)acetonitrile (Example 25, step 1) and by using sodium hydroxide instead of potassium hydroxide.

Step 3: (2RS)-2-(6-Bromo-1-oxo-isoindolin-2-yl)-2-(3-methoxy-2-pyridyl)-N-thiazol-2-yl-acetamide The title compound was obtained as an off-white solid, MS: m/e=458.9/460.9 (M+H$^+$), using chemistry similar to that described in Example 16, step 3 starting from sodium (2RS)-2-(6-bromo-1-oxo-isoindolin-2-yl)-2-(3-methoxy-2-pyridyl)acetate (Example 25, step 2) and thiazol-2-amine.

Step 4: (2RS)-2-[6-[2-(6-Amino-3-pyridyl)ethynyl]-1-oxo-isoindolin-2-yl]-2-(3-methoxy-2-pyridyl)-N-thiazol-2-yl-acetamide The title compound was obtained as a light brown solid, MS: m/e=495.1 (M+H$^+$), using chemistry similar to that described in Example 16, step 4 starting from (2RS)-2-(6-bromo-1-oxo-isoindolin-2-yl)-2-(3-methoxy-2-pyridyl)-N-thiazol-2-yl-acetamide (Example 25, step 3) and 5-ethynylpyridin-2-amine (CAS 82454-61-3).

Step 5: (2RS)-2-[6-[2-(6-Amino-3-pyridyl)ethynyl]-1-oxo-isoindolin-2-yl]-2-(3-hydroxy-2-pyridyl)-N-thiazol-2-yl-acetamide trifluoroacetate The title compound was obtained as a white solid, MS: m/e=481.3 (M+H$^+$), using chemistry similar to that described in Example 15, step 5 starting from (2RS)-2-[6-[2-(6-amino-3-pyridyl)ethynyl]1-oxo-isoindolin-2-yl]-2-(3-methoxy-2-pyridyl)-N-thiazol-2-yl-acetamide (Example 25, step 4) and purifing by reverse chromatography (C18 column, 10% to 90% acetonitrile in water+0.1% trifluoroacetic acid).

Example 26

(2RS)-2-(5-Fluoro-2-hydroxy-phenyl)-2-[7-fluoro-1-oxo-6-[2-(3-pyridyl)ethynyl]isoindolin-2-yl]-N-thiazol-2-yl-acetamide Step 1: Ethyl 3-bromo-6-(bromomethyl)-2-fluorobenzoate The title compound was obtained as a colorless oil using chemistry similar to that described in Example 23, step 1 starting from ethyl 3-bromo-2-fluoro-6-methylbenzoate and by using methyl acetate as solvent.

Step 2: (2RS)-2-(6-Bromo-7-fluoro-1-oxo-isoindolin-2-yl)-2-(5-fluoro-2-methoxy-phenyl)-N-thiazol-2-yl-acetamide The title compound was obtained as a white solid, MS: m/e=494.1/496.1 (M+H$^+$), using chemistry similar to that described in Example 1, step 3 starting from (2RS)-2-amino-2-(5-fluoro-2-methoxyphenyl)-N-(thiazol-2-yl)acetamide hydrochloride (Example 15, step 2) and ethyl 3-bromo-6-(bromomethyl)-2-fluorobenzoate (Example 26, step 1).

Step 3: (2RS)-2-(5-Fluoro-2-hydroxy-phenyl)-2-[7-fluoro-1-oxo-6-[2-(3-pyridyl)ethynyl]isoindolin-2-yl]-N-thiazol-2-yl-acetamide The title compound was obtained as a white solid, MS: m/e=503.2 (M+H$^+$), using chemistry similar to that described in Example 1, step 4 and Example 15, step 5 starting from (2RS)-2-(6-bromo-7-fluoro-1-oxo-isoindolin-2-yl)-2-(5-fluoro-2-methoxy-phenyl)-N-thiazol-2-yl-acetamide (Example 26, step 2) and 3-ethynylpyridine.

Example 27

(2RS)-2-(5-Fluoro-2-hydroxy-phenyl)-2-[6-[2-[4-(morpholinomethyl)phenyl]ethynyl]-1-oxo-isoindolin-2-yl]-N-thiazol-2-yl-acetamide Step 1: (2RS)-2-(5-Fluoro-2-methoxy-phenyl)-2-[6-[2-(4-formylphenyl)ethynyl]-1-oxo-isoindolin-2-yl]-N-thiazol-2-yl-acetamide The title compound was obtained as a light brown solid, MS: m/e=526.3 (M+H$^+$), using chemistry similar to that described in Example 16, step 4 starting from (2RS)-2-(6-bromo-1-oxo-isoindolin-2-yl)-2-(5-fluoro-2-methoxy-phenyl)-N-thiazol-2-yl-acetamide (Example 16, step 3) and 4-ethynylbenzaldehyde (CAS 63697-96-1).

Step 2: (2RS)-2-(5-Fluoro-2-methoxy-phenyl)-2-[6-[2-[4-(morpholinomethyl)phenyl]ethynyl]-1-oxo-isoindolin-2-yl]-N-thiazol-2-yl-acetamide The title compound was obtained as a white foam, MS: m/e=597.4 (M+H$^+$), using chemistry similar to that described in Example 10, step 1 starting from (2RS)-2-(5-fluoro-2-methoxy-phenyl)-2-[6-[2-(4-formylphenyl)ethynyl]-1-oxo-isoindolin-2-yl]-N-thiazol-2-yl-acetamide (Example 27, step 1) and morpholine.

Step 3: (2RS)-2-(5-Fluoro-2-hydroxy-phenyl)-2-[4-[4-[4-(morpholinomethyl)phenyl]ethynyl]-1-oxo-isoindolin-2-yl]-N-thiazol-2-yl-acetamide The title compound was obtained as a white solid, MS: m/e=583.4 (M+H$^+$), using chemistry similar to that described in Example 15, step 5 starting from (2RS)-2-(5-fluoro-2-methoxy-phenyl)-2-[6-[4-(morpholinomethyl)phenyflethynyl]-1-oxo-isoindolin-2-yl]-N-thiazol-2-yl-acetamide (Example 27, step 2).

Example 28

(2RS)-2-(5-Fluoro-2-hydroxy-phenyl)-2-[6-[2-[4-1(4-hydroxy-1-piperidyl)methyl]phenyllethynyl]-1-oxo-isoindolin-2-yl]-N-thiazol-2-yl-acetamide Step 1: (2RS)-2-(5-Fluoro-2-methoxy-phenyl)-2-[6-[2-[4-[(4-hydroxy-1-piperidyl)methyl]phenyl]ethynyl]-1-oxo-isoindolin-2-yl]-N-thiazol-2-yl-acetamide The title compound was obtained as a white foam, MS: m/e=611.5 (M+H$^+$), using chemistry similar to that described in Example 10, step 1 starting from (2RS)-2-(5-fluoro-2-methoxy-phenyl)-2-[6-[2-(4-formylphenyl)ethynyl]-1-oxo-isoindolin-2-yl]-N-thiazol-2-yl-acetamide (Example 27, step 1) and piperidin-4-ol (CAS 5382-16-1).

Step 2: (2RS)-2-(5-Fluoro-2-hy droxy-phenyl)-2-[6-[2-[4-[(4-hydroxy-1-piperidyl)methyl]phenyl]ethynyl]-1-oxo-isoindolin-2-yl]-N-thiazol-2-yl-acetamide The title compound was obtained as a white solid, MS: m/e=597.4 (M+H$^+$), using chemistry similar to that described in Example 15, step 5 starting from (2RS)-2-(5-fluoro-2-methoxy-phenyl)-2-[6-[2-[4-[(4-hydroxy-1-piperidyl)methyl]phenyl]ethynyl]-1-oxo-isoindolin-2-yl]-N-thiazol-2-yl-acetamide (Example 28, step 1).

Example 29

(2RS)-2-(5-Fluoro-2-hydroxy-phenyl)-2-[1-oxo-6-[2-[4-(piperazin-1-ylmethyl)phenyl]ethynyl]isoindolin-2-yl]-N-thiazol-2-yl-acetamide Step 1: tert-Butyl 4-[[4-[2-[43-oxo-2-[(1RS)-1-(5-fluoro-2-methoxy-phenyl)-2-oxo-2-(thiazol-2-ylamino)ethyl]isoindolin-5-yl]ethynyl]phenyl]methyl]piperazine-1-carboxylate The title compound was obtained as an off-white foam, MS: m/e=696.7 (M+H$^+$), using chemistry similar to that described in Example 16, step 4 starting from (2RS)-2-(6-bromo-1-oxo-isoindolin-2-yl)-2-(5-fluoro-2-methoxy-phenyl)-N-thiazol-2-yl-acetamide (Example 16, step 3) and tert-butyl 4-[(4-ethynylphenyl)methyl]piperazine-1-carboxylate (Example 10, step 1).

Step 2: (2RS)-2-(5-Fluoro-2-methoxy-phenyl)-2-[1-oxo-6-[2-[4-(piperazin-1-ylmethyl)phenyl]ethynyl]isoindolin-2-yl]-N-thiazol-2-yl-acetamide tert-Butyl 4-[[4-[2-[3-oxo-2-[(1RS)-1-(5-fluoro-2-methoxy-phenyl)-2-oxo-2-(thiazol-2-ylamino)ethyl]isoindolin-5-yl]ethynyl]phenyl]methyl]piperazine-1-carboxylate (Example 29, step 1) (248 mg, 0.356 mmol) was combined with 9 ml of methanol. HCl (4N in dioxane) (891 µl, 3.56 mmol, 10 equiv.) was added. The reaction mixture was stirred at room temperature for 16 hours. The reaction mixture was evaporated to dryness. The residue was diluted with water, poured into saturated NaHCO$_3$-solution and extracted three times with a mixture of dichloromethane: methanol (9:1). The organic layers were combined, dried over sodium sulfate, filtered and evaporated to dryness to obtain the desired (2RS)-2-(5-fluoro-2-methoxy-phenyl)-2-

[1-oxo-6-[4-[4-(piperazin-1-ylmethyl)phenyl]ethynyl]isoindolin-2-yl]-N-thiazol-2-yl-acetamide (quantitative yield) as an off-white foam, MS: m/e=596.5 (M+H$^+$).

Step 3: (2RS)-2-(5-Fluoro-2-hydroxy-phenyl)-2-[1-oxo-6-[2-[4-(piperazin-1-ylmethyl)phenyl]ethynyl]isoindolin-2-yl]-N-thiazol-2-yl-acetamide The title compound was obtained as a white solid, MS: m/e=582.4 (M+H$^+$), using chemistry similar to that described in Example 15, step 5 starting from (2RS)-2-(5-fluoro-2-methoxy-phenyl)-2-[1-oxo-6-[2-[4-(piperazin-1-ylmethyl)phenyl]ethynyl]isoindolin-2-yl]-N-thiazol-2-yl-acetamide (Example 29, step 2).

Example 30

(2RS)-2-(5-Fluoro-2-hydroxy-phenyl)-2-[6-[2-[4-1(4-methylpiperazin-1-yl)methyl]phenyl]ethynyl]-1-oxo-isoindolin-2-yll-N-thiazol-2-yl-acetamide Step 1: (2RS)-2-(5-Fluoro-2-methoxy-phenyl)-2-[6-[2-[4-[(4-methylpiperazin-1-yl)methyl]phenyl]ethynyl]-1-oxo-isoindolin-2-yl]-N-thiazol-2-yl-acetamide The title compound was obtained as an orange solid, MS: m/e=610.4 (M+H$^+$), using chemistry similar to that described in Example 10, step 1 starting from (2RS)-2-(5-fluoro-2-methoxy-phenyl)-2-[6-[2-(4-formylphenyl)ethynyl]-1-oxo-isoindolin-2-yl]-N-thiazol-2-yl-acetamide (Example 27, step 1) and 1-methylpiperazine (CAS 109-01-3).

Step 2: (2RS)-2-(5-Fluoro-2-hydroxy-phenyl)-2-[6-[2-[4-[(4-methylpiperazin-1-yl)methyl]phenyl]ethynyl]-1-oxo-isoindolin-2-yl]-N-thiazol-2-yl-acetamide The title compound was obtained as a white solid, MS: m/e=596.3 (M+H$^+$), using chemistry similar to that described in Example 15, step 5 starting from (2RS)-2-(5-fluoro-2-methoxy-phenyl)-2-[6-[2-[4-[(4-methylpiperazin-1-yl)methyl]phenyl]ethynyl]-1-oxo-isoindolin-2-yl]-N-thiazol-2-yl-acetamide (Example 30, step 1).

Example 31

(2RS)-2-[6-[2-[4-1(4-Ethylpiperazin-1-yl)methyl]phenyl]ethynyl1-1-oxo-isoindolin-2-yl]-2-(5-fluoro-2-hydroxy-phenyl)-N-thiazol-2-yl-acetamide Step 1: (2RS)-2-[6-[2-[4-[(4-Ethylpiperazin-1-yl)methyl]phenyl]ethynyl]-1-oxo-isoindolin-2-yl]-2-(5-fluoro-2-methoxy-phenyl)-N-thiazol-2-yl-acetamide The title compound was obtained as a light yellow solid, MS: m/e=624.4 (M+H$^+$), using chemistry similar to that described in Example 10, step 1 starting from (2RS)-2-(5-fluoro-2-methoxy-phenyl)-2-[6-[2-(4-formylphenyl)ethynyl]-1-oxo-isoindolin-2-yl]-N-thiazol-2-yl-acetamide (Example 27, step 1) and 1-ethylpiperazine (CAS 5308-25-8).

Step 2: (2RS)-2-[6-[2-[(4-Ethylpiperazin-1-yl)methyl]phenyflethynyl]-1-oxo-isoindolin-2-yl]-2-(5-fluoro-2-hydroxyphenyl)-N-thiazol-2-yl-acetamide The title compound was obtained as a white solid, MS: m/e=610.3 (M+H$^+$), using chemistry similar to that described in Example 15, step 5 starting from (2RS)-2-[6-[2-[4-[(4-ethylpiperazin-1-yl)methyl]phenyl]ethynyl]-1-oxo-isoindolin-2-yl]-2-(5-fluoro-2-methoxy-phenyl)-N-thiazol-2-yl-acetamide (Example 31, step 1).

[1] Yarden, Y., Sliwkowski, M X. Untangling the ErbB signalling network. Nature Review Mol Cell Biol. 2001 Feb; 2(2): 127-37

[2] Ciardiello, F., and Tortora, G. (2008). EGFR antagonists in cancer treatment. The New England journal of medicine 358, 1160-1174

[3] Paez, J. et al. (2004). EGFR mutations in lung cancer: correlation with clinical response to gefitinib therapy. Science (New York, N.Y. 304, 1497-1500

[4] Sharma S V, Bell D W, Settleman J, Haber D A. Epidermal growth factor receptor mutations in lung cancer. Nat Rev Cancer. 2007 Mar;7(3): 169-81

[5] Thress, K. S. et al. Acquired EGFR C797S mutation mediates resistance to AZD9291 in non-small cell lung cancer harboring EGFR T790M. Nat. Med. 21, 560-562 (2015)

[6] Wang et al. EGFR C797S mutation mediates resistance to third-generation inhibitors in T790M-positive non-small cell lung cancer, J Hematol Oncol. 2016; 9: 59

[7] Yang et al, Investigating Novel Resistance Mechanisms to Third-Generation EGFR Tyrosine Kinase Inhibitor Osimertinib in NonSmall Cell Lung Cancer Patients, Clinical Cancer Research, DOI: 10.1158/1078-0432.CCR-17-2310

[8] Jia et al. Overcoming EGFR(T790M) and EGFR(C797S) resistance with mutant-selective allosteric inhibitors, June 2016, Nature 534, 129-132

[9] WO2009158369

[10] WO2016183534

[11] Biochem. Pharmacol. (1973) 22:3099

We claim:
1. A compound of formula I,

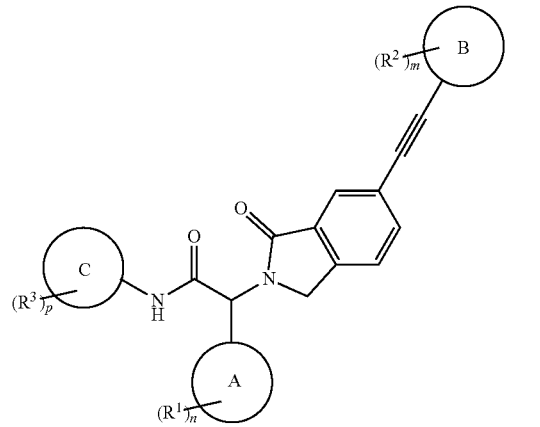

wherein
A is aryl or heteroaryl,
B is aryl or heteroaryl,
C is heteroaryl,
$R^1$ is each independently selected from the group consisting of
  i) amino,
  ii) $C_{1-6}$-alkyl,
  iii) $C_{1-6}$-alkoxy,
  iv) cyano,
  v) halogen,
  vi) halogen-$C_{1-6}$-alkyl,
  vii) halogen-$C_{1-6}$-alkoxy, and
  viii) hydroxy;
$R^2$ is each independently selected from the group consisting of
  i) —(CH$_2$)$_k$—N(R$^4$)(R$^5$),
  ii) —(C=O)—N(R$^4$)(R$^5$), iii) halogen,
iv) —NH—(C=O)—$C_{1-6}$-alkyl, and
v) $C_{1-6}$-alkyl;
$R^3$ is each independently selected from the group consisting of
i) amino,
ii) $C_{1-6}$-alkyl,
iii) $C_{1-6}$-alkoxy,
iv) cyano,
v) halogen,
vi) halogen-$C_{1-6}$-alkyl,
vii) halogen-$C_{1-6}$-alkoxy, and
viii) hydroxy;
$R^4$ is each independently selected from the group consisting of
i) H, and
ii) $C_{1-6}$-alkyl;
$R^5$ is each independently selected from the group consisting of
i) H,
ii) $C_{1-6}$-alkyl, and
iii) —(C=O)—$C_{1-6}$-alkyl;
or $R^4$ and $R^5$ form together with the N they are attached to a heterocyclyl, which heterocyclyl is optionally substituted with $R^6$;
$R^6$ is each independently selected from the group consisting of
i) —OH,
ii) $C_{1-6}$-alkyl, and
iii) —(C=O)—$C_{1-6}$-alkyl;
k is 0, 1 or 2,
n is 0, 1, 2 or 3;
m is 0, 1 or 2; and
p is 0 or 1;
or a pharmaceutically acceptable salt thereof.

2. The compound of claim 1 or a pharmaceutically acceptable salt thereof, wherein:
A is aryl or heteroaryl,
B is aryl or heteroaryl,
C is heteroaryl,
$R^1$ is each independently selected from the group consisting of
i) amino,
ii) $C_{1-6}$-alkyl,
iii) $C_{1-6}$-alkoxy,
iv) cyano,
v) halogen,
vi) halogen-$C_{1-6}$-alkyl,
vii) halogen-$C_{1-6}$-alkoxy, and
viii) hydroxy;
$R^2$ is each independently selected from the group consisting of
i) —$(CH_2)_k$—N($R^4$)($R^5$),
ii) —(C=O)—N($R^4$)($R^5$),
iii) —NH—(C=O)—$C_{1-6}$-alkyl, and
iv) $C_{1-6}$-alkyl;
$R^3$ is each independently selected from the group consisting of
i) amino,
ii) $C_{1-6}$-alkyl,
iii) $C_{1-6}$-alkoxy,
iv) cyano,
v) halogen,
vi) halogen-$C_{1-6}$-alkyl,
vii) halogen-$C_{1-6}$-alkoxy, and
viii) hydroxy;
$R^4$ is each independently selected from the group consisting of
i) H, and
ii) $C_{1-6}$-alkyl;
$R^5$ is each independently selected from the group consisting of
i) H,
ii) $C_{1-6}$-alkyl, and
iii) —(C=O)—$C_{1-6}$-alkyl;
or $R^4$ and $R^5$ form together with the N they are attached to a heterocyclyl;
k is 0, 1 or 2;
n is 0, 1, 2 or 3;
m is 0, 1 or 2; and
p is 0 or 1.

3. The compound of claim 1, or a pharmaceutically acceptable salt thereof, wherein A is aryl.

4. The compound of claim 1, or a pharmaceutically acceptable salt thereof, wherein A is phenyl.

5. The compound of claim 1, or a pharmaceutically acceptable salt thereof, wherein B is aryl.

6. The compound of claim 1, or a pharmaceutically acceptable salt thereof, wherein B is phenyl.

7. The compound of claim 1, or a pharmaceutically acceptable salt thereof, wherein B is heteroaryl.

8. The compound of claim 1, or a pharmaceutically acceptable salt thereof, wherein B is pyridinyl.

9. The compound of claim 1, or a pharmaceutically acceptable salt thereof, wherein C is thiazolyl.

10. The compound of claim 1, or a pharmaceutically acceptable salt thereof, wherein n is 0, 1 or 2.

11. The compound of claim 1, or a pharmaceutically acceptable salt thereof, wherein n is 2.

12. The compound of claim 1, or a pharmaceutically acceptable salt thereof, wherein m is 1.

13. The compound of claim 1, or a pharmaceutically acceptable salt thereof, wherein $R^2$ is: —(C=O)-morpholinyl, —(C=O)N(H)($CH_3$), —$CH_2$-(4-methylpiperazinyl), —$CH_2$-(4-acetylpiperazinyl), —$CH_2$-(4-ethylpiperazinyl), —$CH_2$-(4-hydroxy-piperidyl), —$CH_2$-(morpholinyl), —$CH_2NH_2$, —$CH_2$-piperazinyl, Cl, —N(H)(C=$OCH_3$), or —$NH_2$.

14. The compound of claim 1, or a pharmaceutically acceptable salt thereof, wherein the compound is selected from the group consisting of:
(2RS)-2-(5-Fluoro-2-hydroxy-phenyl)-2-[1-oxo-6-(2-phenylethynyl)isoindolin-2-yl]-N-thiazol-2-yl-acetamide,
(2RS)-2-(5-Fluoro-2-hydroxy-phenyl)-2-[1-oxo-6-[2-(3-pyridyl)ethynyl]isoindolin-2-yl]-N-thiazol-2-yl-acetamide,
(2RS)-2-(5-Fluoro-2-hydroxy-phenyl)-2-[1-oxo-6-[2-[4-(piperazin-1-ylmethyl)phenyl]ethynyl]isoindolin-2-yl]-N-thiazol-2-yl-acetamide,
(2RS)-2-(5-Fluoro-2-hydroxy-phenyl)-2-[6-[2-[4-(morpholinomethyl)phenyl]ethynyl]-1-oxo-isoindolin-2-yl]-N-thiazol-2-yl-acetamide,
(2RS)-2-(5-Fluoro-2-hydroxy-phenyl)-2-[6-[2-[4-[(4-hydroxy-1-piperidyl)methyl]phenyl]ethynyl]-1-oxo-isoindolin-2-yl]-N-thiazol-2-yl-acetamide,
(2RS)-2-(5-Fluoro-2-hydroxy-phenyl)-2-[6-[2-[4-[(4-methylpiperazin-1-yl)methyl]phenyl]ethynyl]-1-oxo-isoindolin-2-yl]-N-thiazol-2-yl-acetamide,
(2RS)-2-(5-Fluoro-2-hydroxy-phenyl)-2-[7-fluoro-1-oxo-6-[2-(3-pyridyl)ethynyl]isoindolin-2-yl]-N-thiazol-2-yl-acetamide, (2RS)-2-[1-Oxo-6-(2-phenylethynyl)isoindolin-2-yl]-2-phenyl-N-thiazol-2-yl-acetamide, (2RS)-2-[1-oxo-6-[2-(3-pyridyl)ethynyl]isoindolin-2-yl]-2-phenyl-N-thiazol-2-yl-acetamide, (2RS)-2-[1-Oxo-6-[2-[4-(piperazin-1-ylmethyl)phenyl]ethynyl]isoindolin-2-yl]-2-phenyl-N-thiazol-2-yl-acetamide, (2RS)-2-[6-[2-(2-Aminopyrimidin-5-yl)ethynyl]-1-oxo-isoindolin-2-yl]-2-(5-fluoro-2-hydroxy-phenyl)-N-thiazol-2-yl-acetamide, (2RS)-2-[6-[2-(2-Chloro-4-pyridyl)ethynyl]-1-oxo-isoindolin-2-yl]-2-(5-fluoro-2-hydroxy-phenyl)-N-thiazol-2-yl-acetamide, (2RS)-2-[6-[2-(6-Acetamido-3-pyridyl)ethynyl]-1-oxo-isoindolin-2-yl]-2-phenyl-N-thiazol-2-yl-acetamide, (2RS)-2-[6-[2-(6-Amino-3-pyridyl)ethynyl]-1-oxo-isoindolin-2-yl]-2-phenyl-N-thiazol-2-yl-acetamide, (2RS)-2-[6-[2-(6-Amino-3-pyridyl)ethynyl]-1-oxo-isoindolin-2-yl]-2-(3-fluorophenyl)-N-thiazol-2-yl-acetamide, (2RS)-2-[6-[2-(6-Amino-3-pyridyl)ethynyl]-1-oxo-isoindolin-2-yl]-2-(2,5-difluorophenyl)-N-thiazol-2-yl-acetamide, (2RS)-2-[6-[2-(6-Amino-3-pyridyl)ethynyl]-1-oxo-isoindolin-2-yl]-2-(1,4,5,6-tetrahydrocyclopenta[c]pyrazol-3-yl)-N-thiazol-2-yl-acetamide, (2RS)-2-[6-[2-(6-Amino-3-pyridyl)ethynyl]-1-oxo-isoindolin-2-yl]-2-(5-fluoro-2-hydroxy-phenyl)-N-thiazol-2-yl-acetamide, (2RS)-2-[6-[2-(6-Amino-3-pyridyl)ethynyl]-1-oxo-isoindolin-2-yl]-2-(5-fluoro-2-hydroxy-phenyl)-N-(2-pyridyl)acetamide, (2RS)-2-[6-[2-(6-Amino-3-pyridyl)ethynyl]-1-oxo-isoindolin-2-yl]-2-(5-chloro-2-hydroxy-phenyl)-N-thiazol-2-yl-acetamide, (2RS)-2-[6-[2-(6-Amino-3-pyridyl)ethynyl]-1-oxo-isoindolin-2-yl]-2-(2-hydroxyphenyl)-N-thiazol-2-yl-acetamide, (2RS)-2-[6-[2-(6-Amino-3-pyridyl)ethynyl]-1-oxo-isoindolin-2-yl]-2-(3-hydroxy-2-pyridyl)-N-thiazol-2-yl-acetamide trifluoroacetate, (2RS)-2-[6-[2-(6-Amino-3-pyridyl)ethynyl]-7-methyl-1-oxo-isoindolin-2-yl]-2-(5-fluoro-2-hydroxy-phenyl)-N-thiazol-2-yl-acetamide, (2RS)-2-[6-[2-(6-Amino-3-pyridyl)ethynyl]-7-methyl-1-oxo-isoindolin-2-yl]-2-(5-fluoro-2-hydroxy-phenyl)-N-(2-pyridyl)acetamide, (2RS)-2-[6-[2-[4-(Aminomethyl)phenyl]ethynyl]-1-oxo-isoindolin-2-yl]-2-phenyl-N-thiazol-2-yl-acetamide, (2RS)-2-[6-[2-[4-(Morpholinomethyl)phenyl]ethynyl]-1-oxo-isoindolin-2-yl]-2-phenyl-N-thiazol-2-yl-acetamide, (2RS)-2-[6-[2-[4-[(4-acetylpiperazin-1-yl)methyl]phenyl]ethynyl]-1-oxo-isoindolin-2-yl]-2-phenyl-N-thiazol-2-yl-acetamide, (2RS)-2-[6-[2-[4-[(4-Ethylpiperazin-1-yl)methyl]phenyl]ethynyl]-1-oxo-isoindolin-2-yl]-2-phenyl-N-thiazol-2-yl-acetamide, (2RS)-2-[6-[2-[4-[(4-Ethylpiperazin-1-yl)methyl]phenyl]ethynyl]-1-oxo-isoindolin-2-yl]-2-(5-fluoro-2-hydroxy-phenyl)-N-thiazol-2-yl-acetamide, (2RS)-2-[6-[2-[6-(Morpholine-4-carbonyl)-3-pyridyl]ethynyl]-1-oxo-isoindolin-2-yl]-2-phenyl-N-thiazol-2-yl-acetamide, and N-Methyl-5-[2-[3-oxo-2-[(1RS)-2-oxo-1-phenyl-2-(thiazol-2-ylamino)ethyl]isoindolin-5-yl]ethynyl]pyridine-2-carboxamide.

15. A method for the treatment of a patient with an EGFR-activated cancer, comprising administering to the patient a therapeutically effective amount of a compound of claim 1, or a pharmaceutically acceptable salt thereof, to the patient.

16. The method of claim 15, wherein the cancer is non-small-cell lung cancer.

17. The method of claim 15, wherein the patient has an EGFR activating mutation.

18. The method of claim 15, further comprising confirming that the patient has an EGFR activating mutation, prior to administering the compound.

19. A pharmaceutical composition comprising a compound of claim 1, or a pharmaceutically acceptable salt thereof, and a pharmaceutically acceptable auxiliary substance.

20. The method of claim 15, wherein the EGFR-activated cancer is selected from colorectal cancer, pancreatic cancer, glioma, head and neck cancer, and lung cancer.

21. The method of claim 15, wherein the EGFR-activated cancer is non-small cell lung cancer.

* * * * *